United States Patent
Barmore et al.

(10) Patent No.: US 12,271,064 B2
(45) Date of Patent: Apr. 8, 2025

(54) EYE SHIELD

(71) Applicant: Gentex Corporation, Simpson, PA (US)

(72) Inventors: Christopher Kent Barmore, Arlington, MA (US); Nathan Winters, Merrimack, NH (US)

(73) Assignee: GENTEX CORPORATION, Simpson, PA (US)

(*) Notice: Subject to any disclaimer, the term of this patent is extended or adjusted under 35 U.S.C. 154(b) by 554 days.

(21) Appl. No.: 17/670,129

(22) Filed: Feb. 11, 2022

(65) Prior Publication Data

US 2022/0260858 A1 Aug. 18, 2022

Related U.S. Application Data

(60) Provisional application No. 63/148,734, filed on Feb. 12, 2021.

(51) Int. Cl.
*G02C 7/16* (2006.01)

(52) U.S. Cl.
CPC ..................... *G02C 7/16* (2013.01)

(58) Field of Classification Search
CPC .......... G02C 7/16; G02C 7/088; G02B 5/003; G02B 27/017; G02B 23/125; G02B 23/16; A61F 9/045
See application file for complete search history.

(56) References Cited

U.S. PATENT DOCUMENTS

| | | | |
|---|---|---|---|
| 2,283,752 A | 5/1942 | Gonsett | |
| 2,986,969 A | 6/1961 | Muncheryan | |
| 4,122,847 A | 10/1978 | Craig | |
| D309,465 S | 7/1990 | Russell | |
| 5,183,059 A | 2/1993 | Leonardi | |
| 5,740,550 A | 4/1998 | Yavitz | |
| 5,769,806 A | 6/1998 | Radow | |
| 5,949,514 A | 9/1999 | Wargon | |
| D424,691 S | 5/2000 | Yavitz | |
| D440,660 S | 4/2001 | Sternberg | |
| D442,693 S | 5/2001 | Sternberg | |
| 6,637,877 B1 | 10/2003 | Hartley et al. | |
| 6,830,331 B2 * | 12/2004 | Jojiki | G02C 7/14 351/158 |

(Continued)

OTHER PUBLICATIONS

Webpage: http://www.fullcompass.com/prod/175266-Sony-3-278-319-01; saved on Dec. 10, 2015.

(Continued)

*Primary Examiner* — James C. Jones
(74) *Attorney, Agent, or Firm* — Morgan, Lewis & Bockius LLP

(57) ABSTRACT

An eye shield has an attachment device configured to be coupled to an optical device. The attachment device includes a clamping ring that has an open position and a closed position. The eye shield further has a shield coupled to the clamping ring to pivot away and towards the clamping ring, the shield extends laterally from the attachment device and a locking element that is disposed on the clamping ring and configured to lock the clamping ring in the closed position. The locking element has a locked and an unlocked position, and when the locking element is in the locked position the clamping ring is in the closed position.

19 Claims, 18 Drawing Sheets

(56) References Cited

U.S. PATENT DOCUMENTS

| | | |
|---|---|---|
| 7,011,404 B2 | 3/2006 | Howard |
| D527,752 S | 9/2006 | Canavan |
| D533,572 S | 12/2006 | Howard |
| D535,394 S | 1/2007 | Johnson |
| 7,542,204 B2 | 6/2009 | Fante et al. |
| D639,441 S | 6/2011 | Sferle |
| D674,903 S | 1/2013 | Harder |
| D723,698 S | 3/2015 | Cockley |
| 9,470,908 B1 | 10/2016 | Frankel et al. |
| 10,061,115 B2 | 8/2018 | Feinbloom et al. |
| 2004/0125444 A1 | 7/2004 | Caplan et al. |
| 2006/0119790 A1 | 6/2006 | Tsai |
| 2012/0033282 A1 | 2/2012 | Immel |
| 2018/0136489 A1 | 5/2018 | Hellstrom |

OTHER PUBLICATIONS

Webpage: http://www.bhphotovideo.com/c/product/616830-REG/Night_Optics_NO_NA_A3144422_Rubber_Eye_Cup.html; saved on Dec. 10, 2015.

Webpage: http://www.bestbinocularsreviews.com/Luna%20Optics1x26LN-EM1-MS-105.htm; saved on Dec. 10, 2015.

International Search Report and Written Opinion dated Jun. 12, 2020 for International Patent Application No. PCT/US2020/012566, 9 pages.

\* cited by examiner

EYE SHIELD

CROSS-REFERENCE TO RELATED APPLICATIONS

This application claims the benefit of U.S. Provisional Patent Application No. 63/148,734 filed Feb. 12, 2021 entitled "Eye Shield", which is incorporated by reference herein in its entirety.

FIELD OF THE INVENTION

The present invention generally relates to an eye shield for use with an optical device and, in some embodiments, to a pair of eye shields for use with night vision goggles (NVGs).

BACKGROUND

Optical devices for enhancing or augmenting a user's vision are used in different environments and for many different purposes. Accessories may be added to the optical devices to aid the user in achieving certain tasks. For example, such accessories may provide additional eye protection to the user.

During use, various optical elements may enhance the vision of the user during activities such as operation of vehicles, including aircrafts, or during military engagement. For example, optical devices, such as night vision goggles, may be used by many individuals in the military to accomplish certain tasks and objectives at night. These optical devices may include head mounted devices. For example, an optical device, such as night vision goggles, may be mounted to a helmet to assist a user in accomplishing tasks during the night or during low light. In some situations, such as military engagement, the use of eye protection is desired to protect the user's eyes from debris and/or light/lasers.

Current eye protection methods include standard safety goggles. However, safety goggles in conjunction with the use of optical devices and night vision goggles do not provide adequate visibility. For example, wearing standard safety goggles behind night vision goggles is not ideal as the user's visibility and perception are affected or may be impaired. Further, when utilizing standard safety goggles, the eyepiece of the night vision goggles is further from the user's eye, thereby affecting their vision through the night vision goggles. Other methods of protecting a user's eyes when using optical devices include the use of standard rubber eyecups around the eyepiece of the night vision goggles. These standard rubber eyecups allow the night vision goggles to be closer to the eye of the user; however, they do not allow for peripheral vision and may not provide adequate protection against lasers/lights, ballistics, and debris. In addition, some current eye protection methods couple to the night vision goggles at the eye piece or the back end (face side). These eye protection methods are not compatible with certain night vision goggles, such as the ANVIS goggles, which have adjustment rings disposed at the back end of the goggles, such as around the eye piece.

BRIEF SUMMARY OF THE INVENTION

In one embodiment, there is an eye shield including an attachment device configured to be coupled to an optical device, the attachment device including a clamping ring having an open position and a closed position, a shield coupled to the clamping ring to pivot away and towards the clamping ring, the shield extending laterally from the attachment device, and a locking element disposed on the clamping ring configured to lock the clamping ring in the closed position, wherein the locking element has a locked and an unlocked position, and the locking element being in the locked position results in the clamping ring being in the closed position.

In some embodiments, the eye shield further includes a coupling mechanism coupling the shield to the clamping ring. The shield may be fixedly coupled to the coupling mechanism. The coupling mechanism may be pivotally coupled to the clamping ring to allow the shield and the coupling mechanism to pivot relative to the clamping ring. The coupling mechanism may be coupled to the clamping ring via at least one pivot pin.

In some embodiments, the locking element includes a channel and an extending member, the channel sized and shaped to receive the extending member. The locking element may include a coupling element coupling the channel to the extending member. The channel may include a lip and the extending member may include a latch, the latch may be configured to receive and secure the lip in place when the extending member is disposed within the channel. The latch may be configured to be actuated by a user to move the locking element from the locked position to the unlocked position.

In some embodiments, the locking element includes a tab extending away from the clamping ring. The locking element may include a lip and a latch, the latch may be configured to secure the lip in place when the locking element is in the locked position.

In some embodiments, the shield is pivotally coupled to the clamping ring. The clamping ring may include an aperture having a diameter, the diameter of the aperture may be greater when the clamping ring is in the open position than when the clamping ring is in the closed position.

In some embodiments, the attachment device and the shield are composed of different materials.

In some embodiments, the shield is optically transparent. The shield may be optically opaque to lasers and/or lights.

In some embodiments, the clamping ring is configured to be disposed around a portion of the optical device, the optical device including one of night vision goggles, binoculars, monocular, scopes, spectacles, augmented reality system, virtual reality system, display devices, or cameras.

In some embodiments, the eye shield further includes a first tether coupled to the attachment device and configured to couple to a second tether coupled to an adjacent attachment device to secure the attachment device to the adjacent attachment device.

Another embodiment of the present invention provides for an eye shield including an attachment device configured to be coupled to an optical device, the attachment device including a clamping ring having an open position and a closed position, and a coupling mechanism pivotally coupled to the clamping ring, a shield coupled to the coupling mechanism and configured to pivot away and towards the clamping ring, the shield extending laterally from the attachment device, and a locking element disposed on the clamping ring configured to lock the clamping ring in the closed position around at least a portion of the optical device, the locking element having a locked and an unlocked position, and the locking element being in the locked position results in the clamping ring being in the closed position, wherein the locking element including a lip and a latch, the latch configured to secure the lip in place when the locking element is in the locked position.

Another embodiment of the present invention provides for an eye shield including an attachment device configured to be coupled to an optical device, the attachment device including a clamping ring having an open position and a closed position, and a coupling mechanism pivotally coupled to the clamping ring, a shield coupled to the coupling mechanism and configured to pivot away and towards the clamping ring, the shield extending laterally from the attachment device and being optically opaque to lasers and/or light, and a locking element disposed on the clamping ring configured to lock the clamping ring in the closed position around the optical device, the locking element having a locked and an unlocked position, the locking element being in the locked position results in the clamping ring being in the closed position, wherein the locking element includes a tab extending from the locking element, a channel having a lip, and an extending member having a latch, the channel sized and shaped to receive the extending member and the latch configured to secure the lip in place when the locking element is in the locked position.

BRIEF DESCRIPTION OF THE DRAWINGS

The following detailed description of embodiments of the eye shield, will be better understood when read in conjunction with the appended drawings of exemplary embodiments. It should be understood, however, that the invention is not limited to the precise arrangements and instrumentalities shown.

In the drawings.

DETAILED DESCRIPTION

Figure 1:
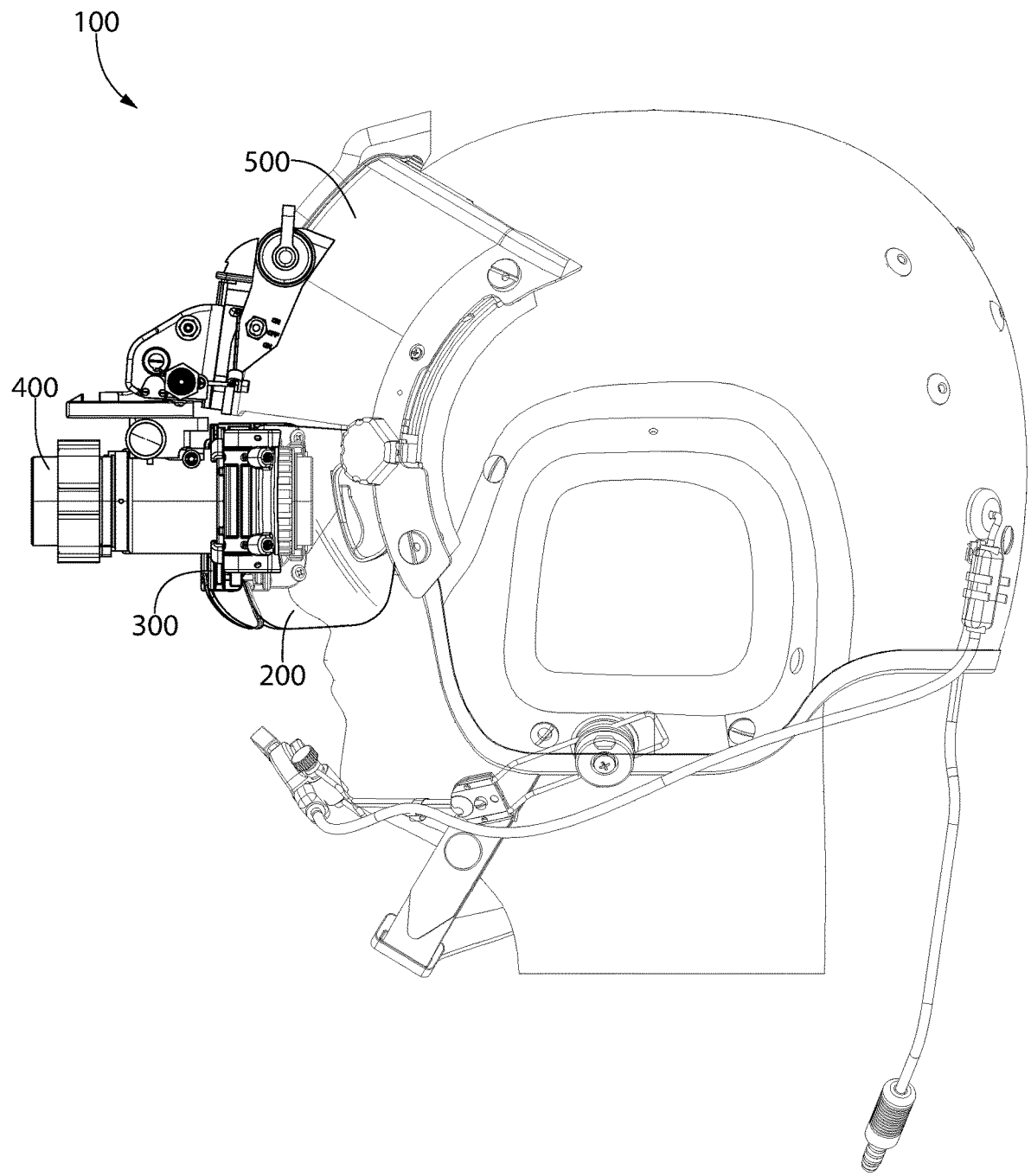
FIG. 1 is a left-side view of a pair of eye shields mounted to an optical device in accordance with an exemplary embodiment of the present invention shown with the optical device mounted to a helmet.

Referring to the drawings in detail, wherein like reference numerals indicate like elements throughout, there is shown in FIGS. 1-13B eye shields, generally designated 100, in accordance with exemplary embodiments of the present invention. Various embodiments of eye shield 100 are described in further detail below in reference to the exemplary embodiments shown in the figures.

Referring to FIGS. 1-4, in use, eye shield 100 may be coupled to an optical device 400, such as night vision goggles, binoculars, monocular, scopes, spectacles, augmented reality systems/displays, virtual reality systems/displays, display devices, and/or cameras, to protect a user's eye(s) from lasers, lights, ballistics, projectiles, and other debris. For example, eye shield 100 may be used by an operator (e.g., pilot) operating a moving vehicle, such a helicopter, to protect the operator from lasers or lights directed towards the vehicle. In some embodiments, eye shield 100 is configured to remain attached to optical device 400 during high wind stream situations, such as during operation of a helicopter, cargo plane, or military aircraft. For example, eye shield 100 may remain coupled to optical device 400 during winds in excess of 160 knots. In some embodiments, eye shield 100 is configured to remain attached to optical device 400 when bumped, such as when eye shield 100 receives contact or an impact. Specifically, eye shield 100 may be coupled to optical device 400 and may be configured to allow for the securement of optical device 400 to eye shield 100 in addition to protection of the user's eyes and surrounding areas of the user's face.

Eye shield 100 may extend radially outwardly from the viewing area of optical device 400 to provide protection from ballistics and debris as well as block out or reduce distracting light, lasers, and/or glare. For example, eye shield 100 may extend laterally from optical device 400, away from the user's eyes and nose, and curve toward the user's temple to prevent debris, lasers, and/or light from entering the user's eye or field-of-view peripherally and from the side. Further, eye shield 100 may provide for an improved method of securing eye shield 100 to optical device 400, preventing eye shield 100 from becoming detached from optical device 400 during activity, while also providing the necessary protection to the user's eyes. Eye shield 100 may also be configured to fold away and towards optical device 400 to allow a user to adjust the location of eye shield 100, provide for easy storage, and/or reduce the footprint of eye shield 100. In some embodiments, eye shield 100 is configured to couple to optical device 400 such that stowing of optical device 400 results in stowing of eye shield 100.

Figure 2:
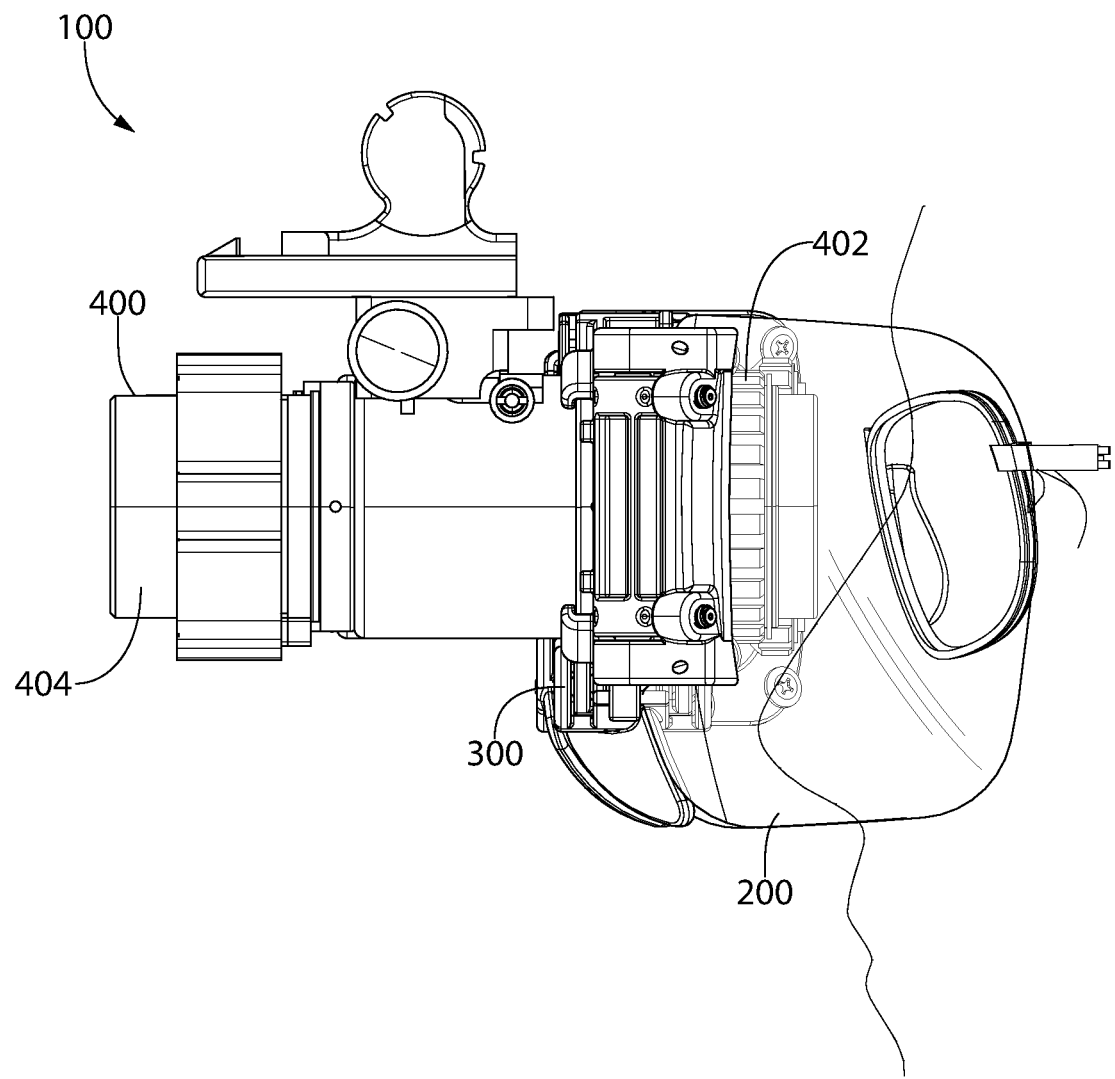
FIG. 2 is a zoomed in view of the pair of eye shields of FIG. 1.

Referring to FIGS. 1-2, eye shield 100 may include shield 200 and attachment device 300. Shield 200 may be coupled to attachment device 300. Attachment device 300 may be configured to secure shield 200 to a portion of optical device 400, such as a portion of tube 406 of optical device 400. For example, optical device 400 may be night vision goggles (also referred to as "NVG") and shield 200 may be secured to the night vision goggles via attachment device 300. In one embodiment, optical device 400 is one of ANVIS (Aviator's Night Vision Imaging System), AN/AVS-6, AN/AVS-9, ANVIS 6, ANVIS 9, 4949, M949, AN/PVS-23, F5050, 5050, or AN/AVS-9 CHMD night vision goggles. However, eye shield 100 may be used with other types of night vision goggles or optical devices. Shield 200 may be pivotally coupled to attachment device 300, which may secure shield 200 to optical device 400. Shield 200 may be pivotally coupled to attachment device 300 such that shield 200 pivots about optical device 400. In some embodiments, attachment device 300 secures shield 200 to optical device 400 at a portion proximate eye piece 402. For example, shield 200 may be pivotally coupled to attachment device 300, which may clamp around a portion of optical device 400 proximate eye piece 402, thereby securing eye shield 100 and shield 200 to optical device 400.

Figure 3:
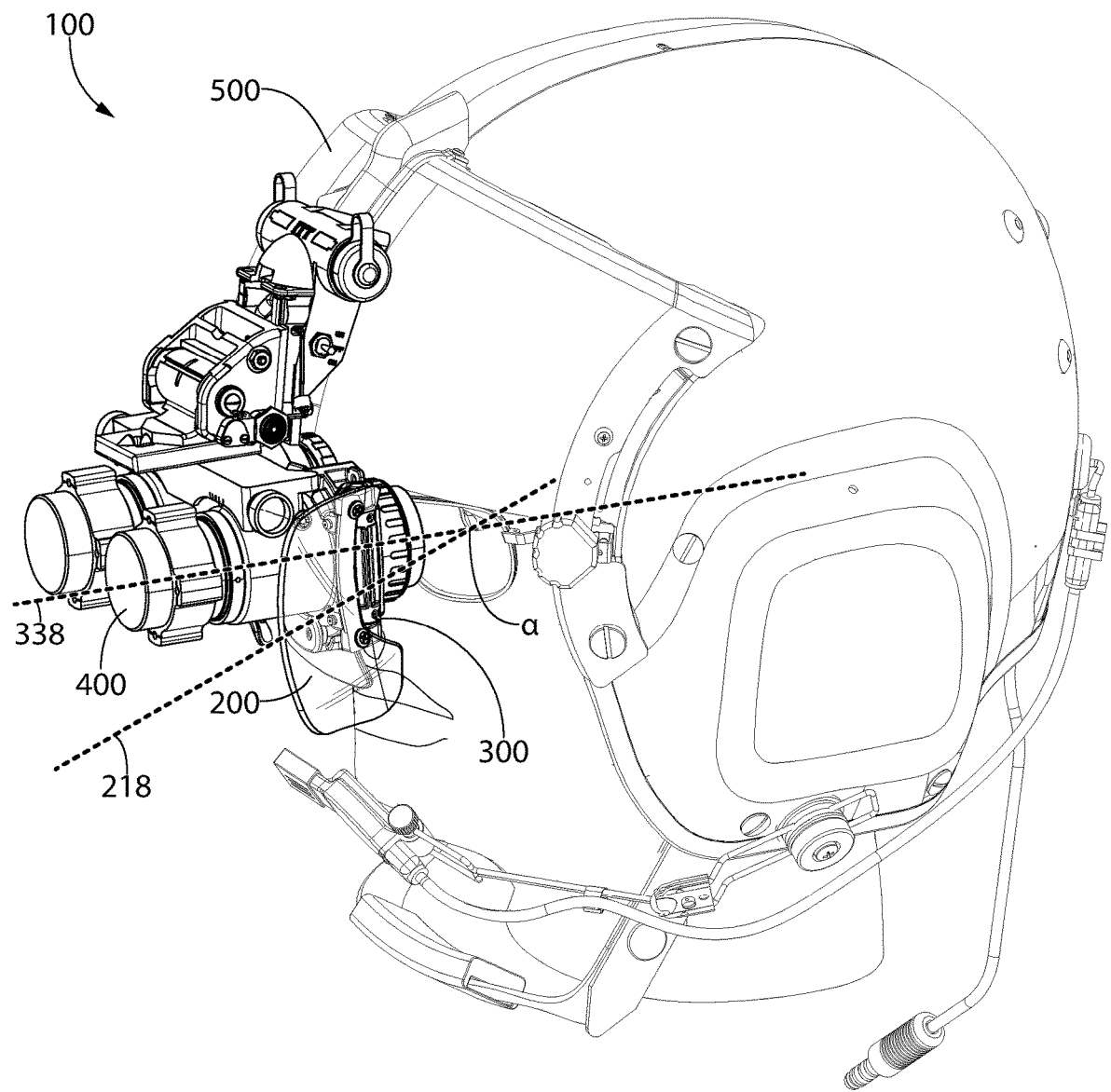
FIG. 3 is a perspective view of the pair of eye shields of FIG. 1 shown with the optical device in the use position.
Figure 4:
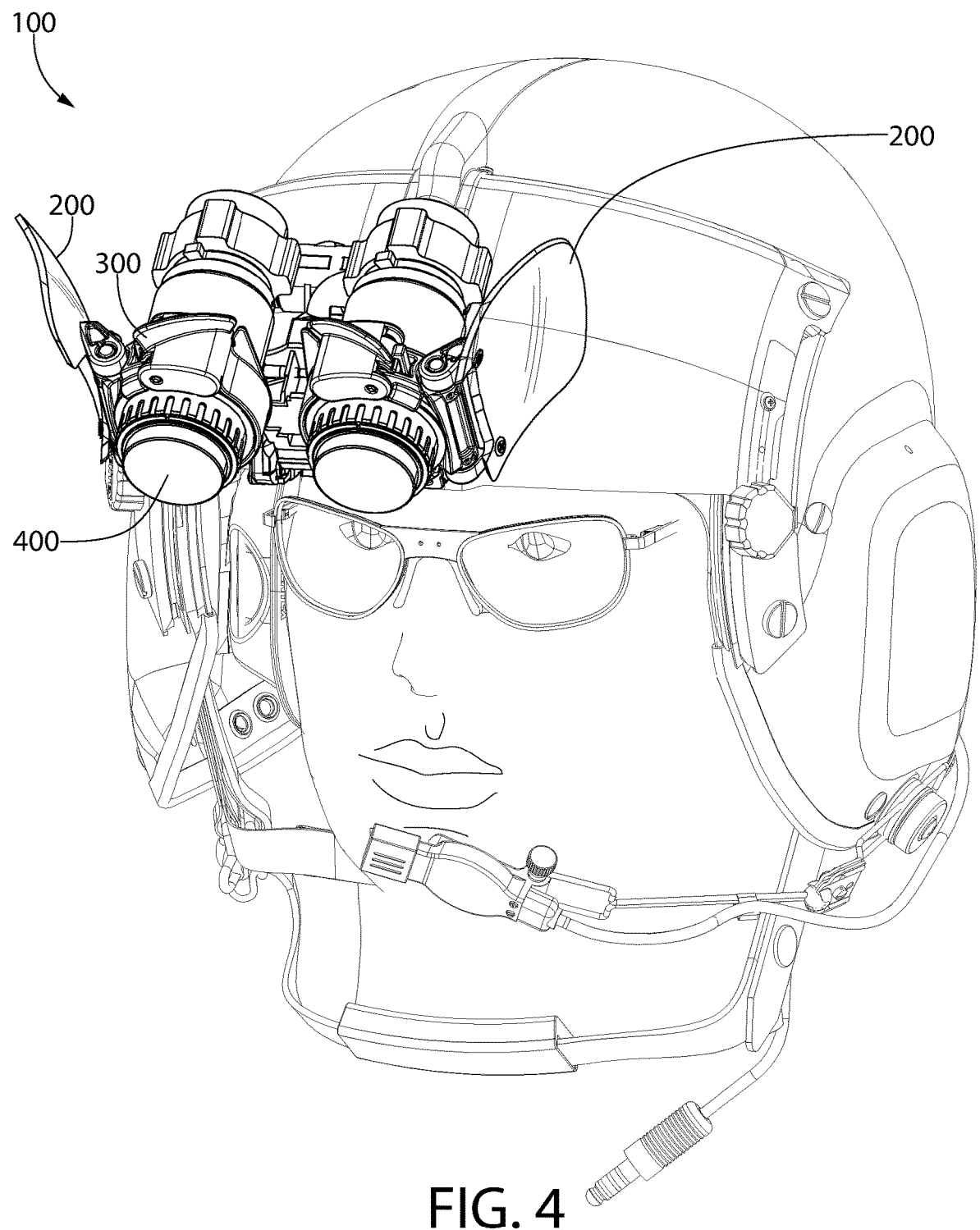
FIG. 4 is a perspective view of the pair of eye shields of FIG. 1 shown with the optical device in the stowed position.

Referring to FIGS. 3 and 4, eye shield 100 may be coupled to optical device 400 via attachment device 300, and optical device 400 may be pivotally coupled to helmet 500 to allow for easy retrieval and removal from the user's line of sight. For example, optical device 400 may be pivotally coupled to helmet 500 such that optical device 400 can be in a use position (see FIG. 3) and a stowed position (see FIG. 4). Eye shield 100 may be coupled to optical device 400 such that movement of optical device 400 from the use position to the stowed position and vice versa causes movement of eye shield 100. In some embodiments, eye shield 100 is coupled to optical device 400 such that movement of optical device 400 results in movement of eye shield 100. Eye shield 100 may be coupled to optical device 400 such that during movement of optical device 400, eye shield 100 remains substantially stationary relative to optical device 400.

In some embodiments, helmet 500 is an advanced combat helmet (ACH), an enhanced combat helmet (ECH), a modular integrated communications helmet (MICH), a tactical ballistic helmet (TBH), a lightweight marine helmet, police general duty helmet, a personnel armor system for ground troops (PASGT), or an aircrew helmet, such as an HGU-56/P rotary wing helmet or an HGU 55/P fixed wing helmet. In some embodiments, more than one eye shield 100 may be provided. For example, a pair of eye shields 100 may be provided for each eye piece 402 of optical device 400, which may include more than one eye piece 402. Each eye shield 100 may be coupled separately to a corresponding eye piece 402. For example, a kit may be provided that includes a pair of eye shields 100 configured to couple to one or more optical devices 400.

Figure 12A:
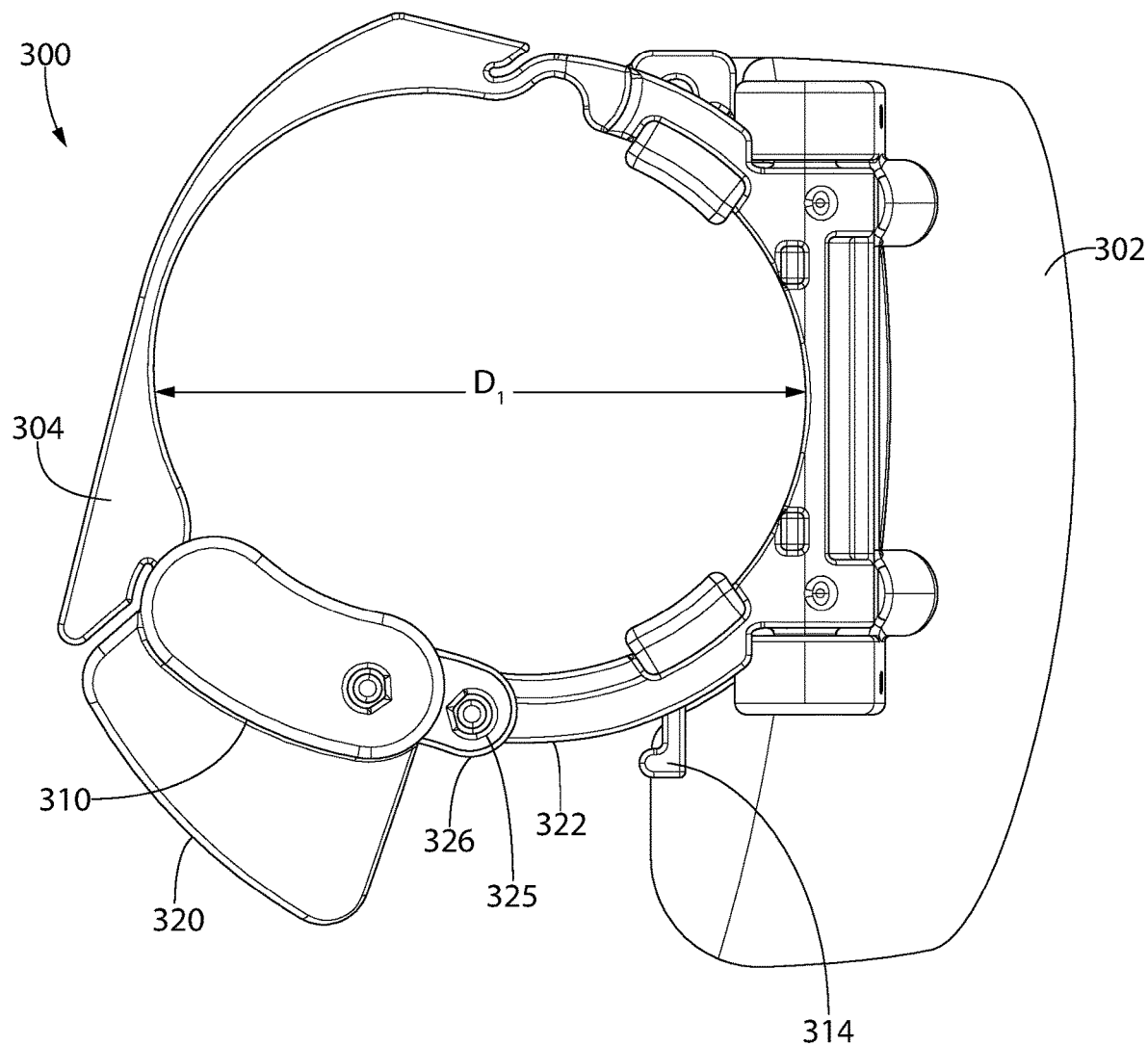
FIG. 12A is a front view of an eye shield of the pair of eye shields of FIG. 1 with the optical device removed and the clamping ring in the open position.
Figure 12B:
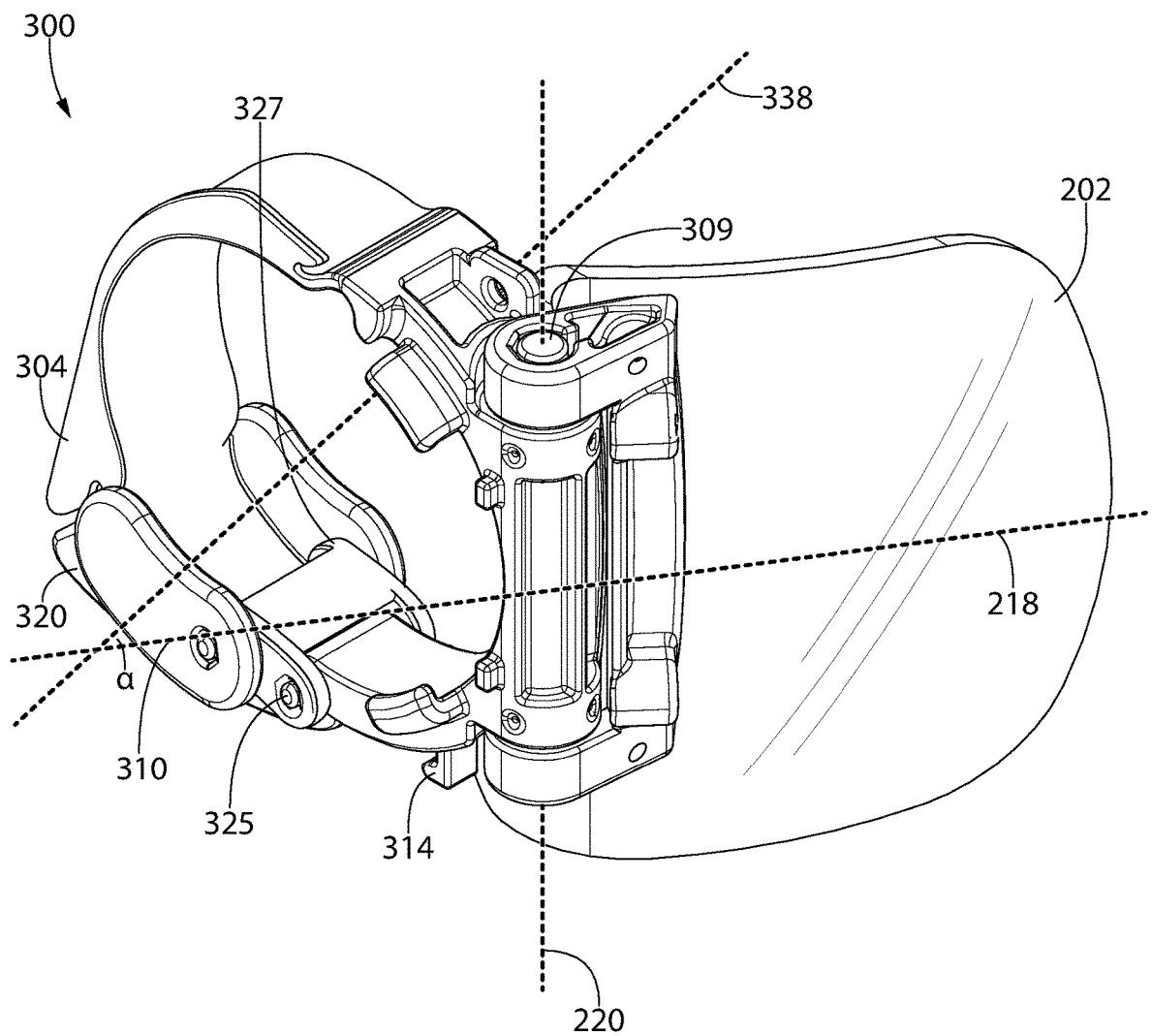
FIG. 12B is a front perspective view of the eye shield of FIG. 12A.

Referring to FIGS. 3 and 12B, attachment device 300 may include central axis 338 and shield 200 may include central axis 218. Central axis 338 of attachment device 300 may extend through the center of attachment device 300. In some embodiments, when attachment device 300 is coupled to optical device 400, central axis 338 extends along the entire length of tube 406. Central axis 218 of shield 200 may extend along the surface of shield 200 and may be perpendicular to pivot axis 220 (e.g., the axis of rotation of shield 200). Central axis 338 and central axis 218 may form angle α. Angle α may be from 0° to approximately 180°. In some embodiments, shield 200 is configured to rotate approximately 150°. Shield 200 may have a range of motion of approximately 150°. In use, moving shield 200 from the stowed position to the use position results in rotating shield 200 approximately 150°. For example, angle α may be approximately 20° when shield 200 is in the use position (see FIG. 12B) and angle α may be approximately 170° when shield 200 is in the stowed position (see FIG. 3).

When shield 200 is in the stowed position (e.g., shield 200 being proximate the tube 406 when attachment device 300 is coupled to optical device 400), as shown in FIG. 3, angel a may be approximately 90° to approximately 180°. For example, angel a may be approximately 100° to approximately 170°, approximately 110° to approximately 160°, or approximately 120° to approximately 150°. In some embodiments, when shield 200 is in the stowed position, angle α is from approximately 150° to approximately 180° (e.g., approximately 170°). When shield 200 is in the use position (e.g., shield 200 being proximate the user's face), as shown in FIG. 12B, angel a may be 0° to approximately 90°. For example, angel a may be approximately 10° to approximately 80°, approximately 20° to approximately 70°, or approximately 30° to approximately 60°. In some embodiments, when shield 200 is in the use position, angle α is from approximately 15° to approximately 45° (e.g., approximately 20°). In some embodiments, moving shield 200 from the stowed position to the use position results in decreasing angle α and moving shield 200 from the use position to the stowed position results in increasing angle α.

In some embodiments, shield 200 is configured to pivot/fold relative to optical device 400. Shield 200 may be configured to fold forward and away from the face of the user. For example, shield 200 may be pivotally coupled to attachment device 300 allowing shield 200 to pivot about attachment device 300. Shield 200 may pivot from being disposed proximate the user's face to being disposed away from the user's face. For example, shield 200 may pivot from being disposed proximate the eye of a user to being proximate optical device 400. Shield 200 being pivotally coupled to attachment device 300 allows optical device 400 to be easily moved from the use position to the stowed position without shield 200 being cumbersome or a snagging hazard. For example, shield 200 may be pivoted such that it is proximate optical device 400 to allow for easy storage of optical device 400 and eye shield 100. Shield 200 pivoting to be proximate optical device 400 reduces the overall size and footprint of optical device 400 when it is coupled to eye shield 100 thereby making it easier to move into the stowed position for storage. Shield 200 being configured to pivot about attachment device 300 also allows the user to flip shield 200 forward when no longer needed.

In some embodiments, shield 200 being configured to flip forward allows eye shield 100 to be less bulky and have a smaller footprint, especially when optical device 400 is in the stowed position. In practice, a user may pivot and fold shield 200 out of the peripheral field-of-view without having to remove eye shield 100 from optical device 400. For example, as shown in FIGS. 3 and 4, optical device 400 may be moved from the use position to the stowed position without removing eye shield 100 from optical device 400. Further, the pivoting and folding of shield 200 prevents shield 200 from being a snagging hazard when optical device 400 is moved from the use position to the stowed position.

In some embodiments, a kit is provided which includes multiple eye shields 100. The kit may include extra eye shields 100, extra shields 200, and/or extra attachment devices 300. Extra eye shields 100, extra shields 200, and/or extra attachment devices 300 may be provided to be used with multiple optical devices 400, for different sized optical devices 400, different applications (e.g., shield 200 having different levels of optically transparency based on the application/desired use), or as replacements due to eye shield 100 being damaged or lost. For example, multiple eye shields 100 of various sizes and shapes may be provided in a single kit such that a user may pick from the appropriate eye shield 100 from the kit. Further, eye shield 100 may be provided in a set or as a pair. In some embodiments, the kit may include two, three, four, five, six, or greater than six eye shields 100 of different sizes and shapes.

Figure 5A:
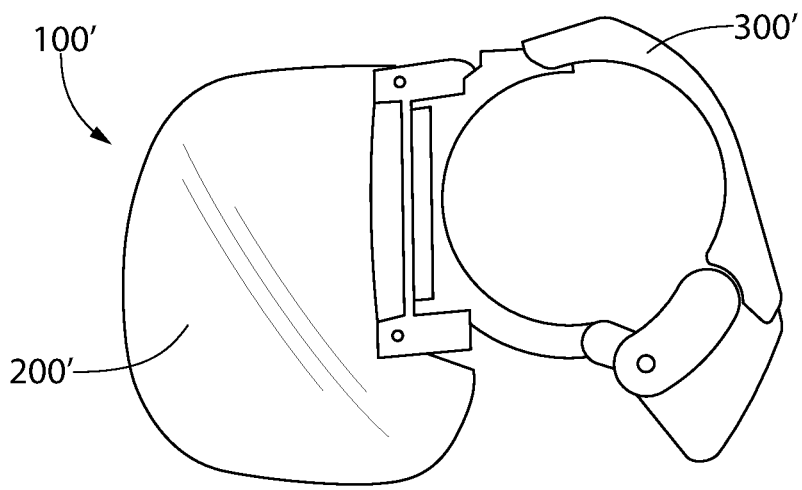
FIGS. 5A-5C are front views of various embodiments of eye shields in accordance with exemplary embodiments of the present invention sized and shaped to fit various optical devices.
Figure 5B:
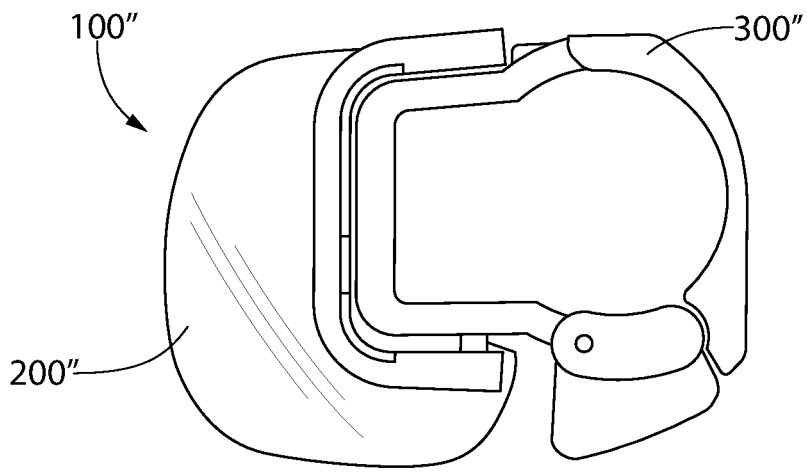
Figure 5C:
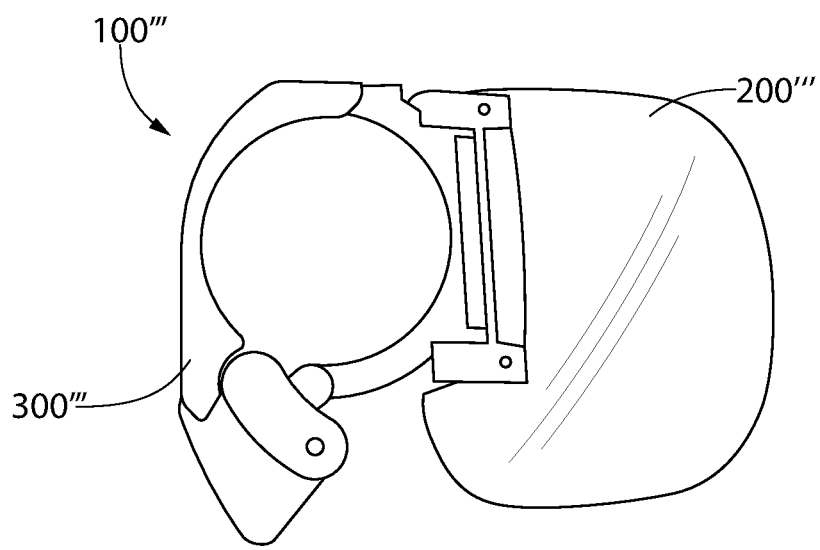

As shown in FIGS. 5A-5C, the kit may include three eye shields 100', 100", and 100'. Each of eye shields 100', 100", and 100' may be individually configured to fit a different optical device. For example, eye shield 100' may be a right shield for use with an AN/AVS-9, eye shield 100" may be a right shield for use with an AN/AVS-9 CHMD, and eye shield 100' may be a left shield for either and AN/AVS-9 or AN/AVS-9 CHMD. In some embodiments, the kit may include multiple sets of multiple eye shields 100, such as 10 sets, to fit different optical devices, such as AN/AVS-9 or AN/AVS-9 CHMD. However, the kit may include 2 sets, 3 sets, 4 sets, 5 sets, greater than 5 sets, or greater than 10 sets of eye shields 100 to fit different optical devices. In some embodiments, eye shield 100' includes shield 200' and attachment device 300', eye shield 100" includes shield 200" and attachment device 300", and eye shield 100''' includes shield 200''' and attachment device 300'''.

The pair of eye shields 100 may be mirror images of each other so that they may be used with each eye piece 402 of optical device 400. The pair of eye shields 100 may be mirror images along the medial plane, i.e., the central line, of optical device 400. However, the pair of eye shields 100 may be each shaped differently. For example, one eye shield 100 of the pair may be notched to allow a firearm to contact the right side of a user's face, e.g., the cheek of a user, while sighting a target. In some embodiments, eye shield 100 may be provided individually to be used with optical device 400 that may include only one eye piece 402.

Figure 6:
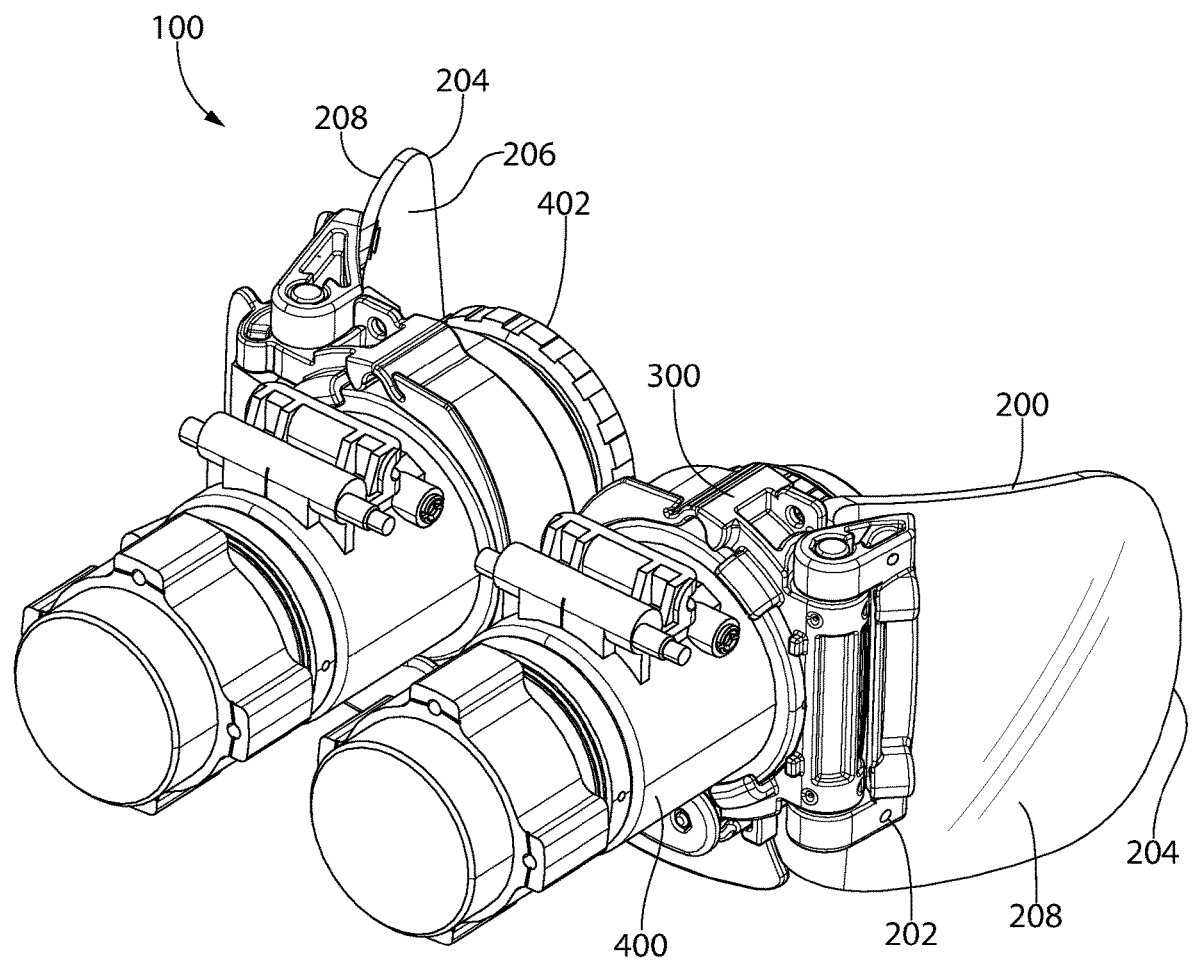
FIG. 6 is a top perspective view of the pair of eye shields of FIG. 1.
Figure 7:
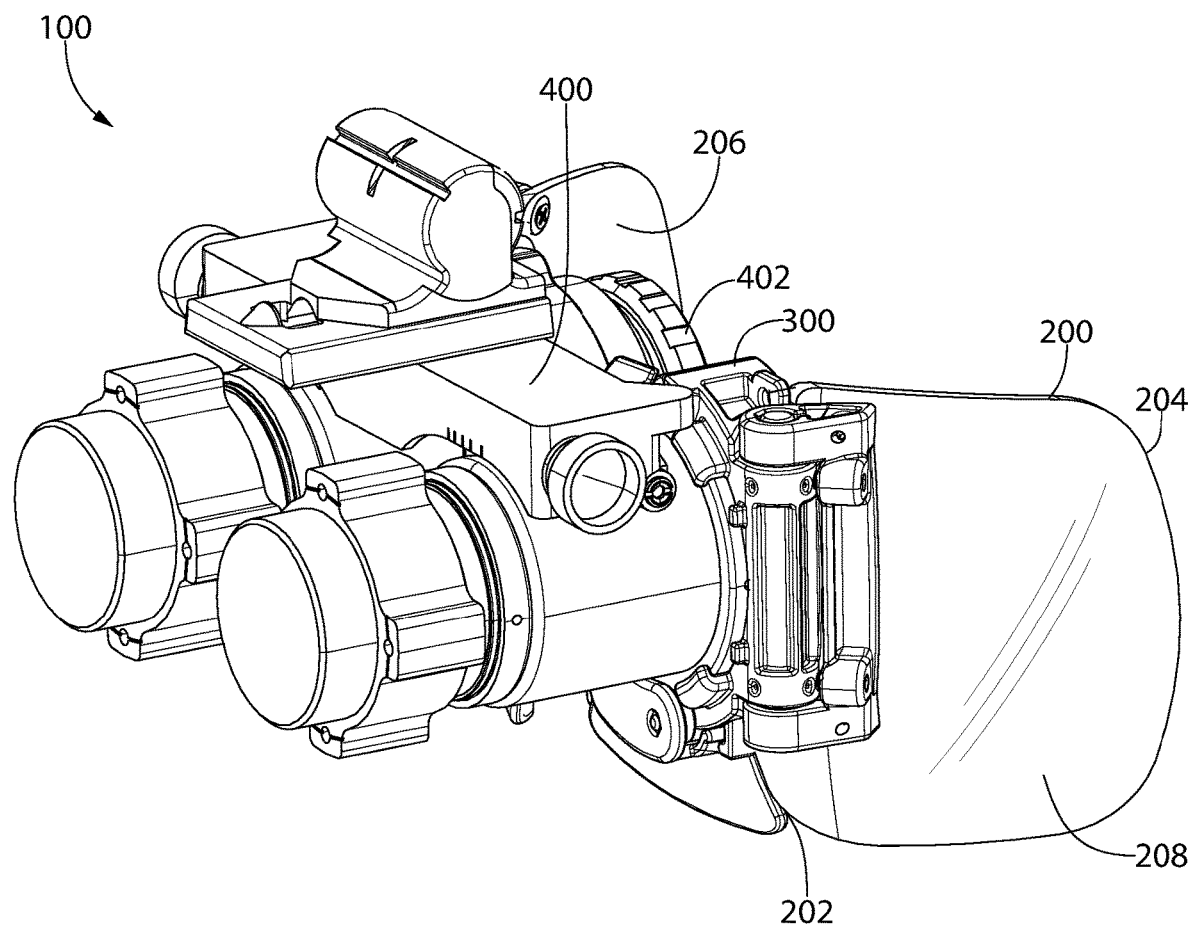
FIG. 7 is a right-side perspective view of the pair of eye shields of FIG. 1.
Figure 8:
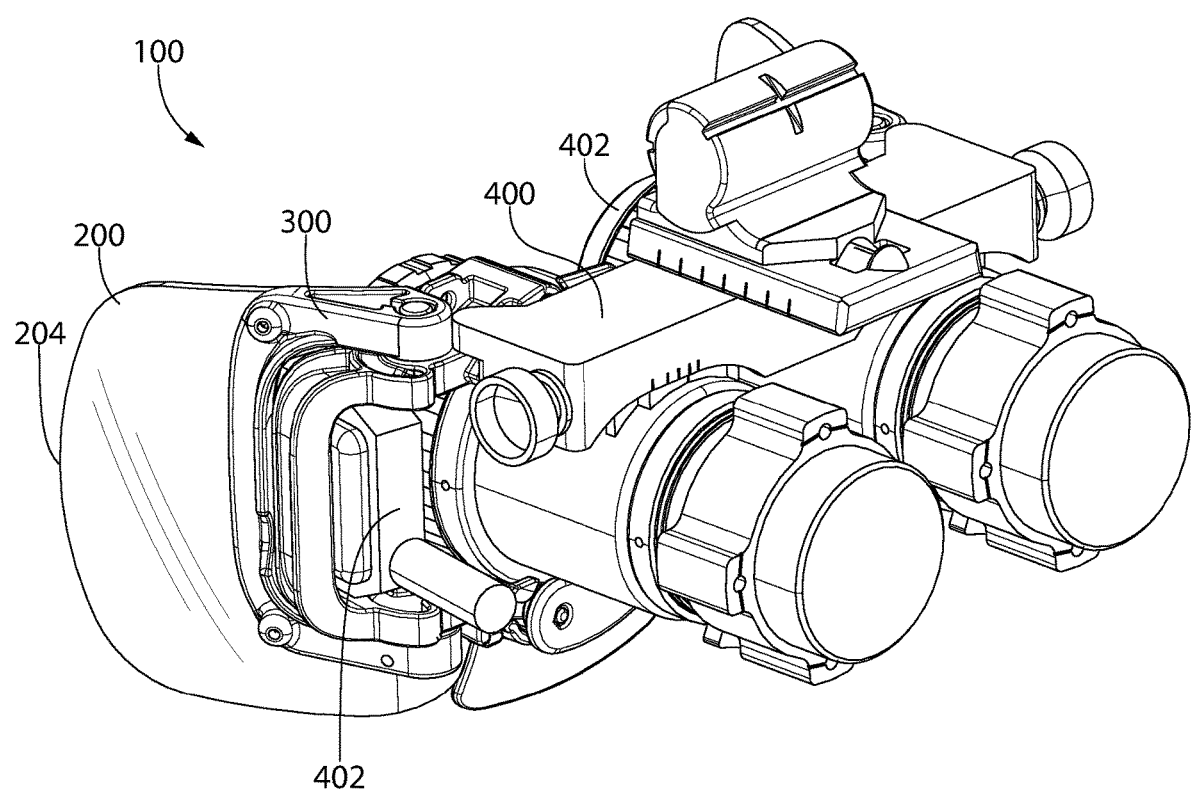
FIG. 8 is a right-side perspective view of the pair of eye shields of FIG. 1.

Referring to FIGS. 6-8, shield 200 may be used to protect the eyes and surrounding area of a user from various debris, projectiles, and/or ballistics. Shield 200 may have proximal end 202 and distal end 204. During use of eye shield 100, shield 200 may be coupled to attachment device 300 at proximal end 202 and distal end 204 of shield 200 may be disposed proximate the user's eyes, cheek, and/or temple. In some embodiments, proximal end 202 of shield 200 is disposed opposite distal end 204.

Shield 200 may extend to cover a substantial portion of a user's face, such as the portion surrounding their eyes. In some embodiments, shield 200 is tapered laterally, away from the user's eyes and nose. For example, shield 200 may taper towards the temple of the user. Shield 200 may taper from proximal end 202 to distal end 204. However, shield 200 may not have any taper or may taper towards the user's eyes and nose. For example, shield 200 may taper from distal end 204 to proximal end 202.

Shield 200 may be configured to extend from attachment device 300. In some embodiments, shield 200 is configured to extend from a portion of attachment device 300. For example, shield 200 may be configured to only couple to a portion of attachment device 300 such that shield 200 does not surround a substantial portion or the entirety of attachment device 300.

In some embodiments, shield 200 is substantially square in shape. However, shield 200 may rectangular, oval, ellipsoidal, circular, triangular, hexagonal, octagonal, or any other shape desired. In some embodiments, shield 200 has rounded corners to prevent shield 200 from being a snagging hazard or causing inadvertent damage to the user's face or hands. Shield 200 may be frameless. However, in some embodiments, shield 200 includes a frame around the periphery of shield 200. Shield 200 may be sized and shaped to provide protection to a user' eyes and surrounding areas. For example, in use, shield 200 may provide peripheral protection to a user's eyes to prevent lasers, lights, and/or debris from entering the user's field-of-vision when the user is using optical device 400.

Shield 200 may have a maximum width of approximately 3 inches, a maximum height of approximately 3 inches, and a maximum thickness of approximately ⅛ inch. In some embodiments, due to curvature of shield 200, shield 200 may have a maximum thickness of approximately ⅜ inch. However, shield 200 may have a maximum width of approximately 1 inch to approximately 8 inches, approximately 2 inches to approximately 6 inches, or approximately 3 inches to approximately 7 inches, a maximum height of approximately 1 inch to approximately 8 inches, approximately 2 inches to approximately 6 inches, or approximately 3 inches to approximately 7 inches, and a maximum thickness of approximately 1/32 inch to approximately 3 inches, approximately ⅛ inch to approximately 2 inches, or approximately ½ inch to approximately 1 inch. In some embodiments, the maximum width, maximum height, and maximum thickness of a shield 200 varies from proximal end 202 to distal end 204. The maximum width, maximum height, and maximum thickness of a shield 200 may vary across different eye shields 100.

In some embodiments, shield 200 limits the amount a user's field of vision is exposed outside of the viewing area of optical device 400. For example, shield 200 may be at least partially opaque thereby limiting the amount a user is able to peripherally view their surroundings or environment. In some embodiments, shield 200 is opaque and not optically transparent to protect the user's eyes against lasers and/or lights. For example, shield 200 may not be optically transparent to visible light or lasers, such as light having wavelength between approximately 350 nm and approximately 750 nm. In some embodiments, shield 200 may not be optically transparent to light having a wavelength between approximately 150 nm and approximately 1 mm. However, shield 200 may be fully transparent to allow a user to have complete field of view, including peripheral view. In some embodiments, shield 200 is configured to provide notifications such as lights or a display to selectively provide information to a user. For example, shield 200 may include a liquid crystal display (LCD), a light emitting diode (LED) display, an organic light emitting diode (OLED) display, or any other type display technology. Shield 200 may be configured to display information or indicators to a user. In some embodiments, all or part of shield 200 is comprised of a display (e.g., LCD, LED, OLED).

In some embodiments, shield 200 includes first surface 206 and second surface 208. First surface 206 may be the surface of shield 200 proximate the user's face when shield 200 is folded towards the user's face and second surface 208 may be the opposite surface to first surface 206. In some embodiments, second surface 208 is the surface of shield 200 furthest from the user's face when shield 200 is folded towards the user's face. One or more of first surface 206 and second surface 208 may be comprised of a display (e.g., LCD, LED, OLED). For example, first surface 206 may be comprised of a display (e.g., LCD, LED, OLED) such that a user may receive information via shield 200.

In some embodiments, shield 200 is comprised of a resilient material. For example, shield 200 may be made of a polycarbonate material or polyester alternatives. However, shield 200 may be comprised of other materials such as metal, steel, polymers, or any other material desired. In some embodiments, shield 200 is comprised of a lightweight material that is also resilient. In some embodiments, shield 200 is substantially rigid. For example, shield 200 may be substantially rigid such that shield 200 can receive an impact or force without bending or flexing toward the user, which may cause injury to the user's face and/or eye. Shield 200 may include the use of laser protective dyes and coatings, light reducing and reflecting dyes and coatings, and integration with anti-scratch, anti-fog, anti-reflection, and/or anti-smudge coatings.

In a preferred embodiment, shield 200 is optically opaque to lasers and/or lights. However, shield 200 may have any level of transparency. For example, shield 200 may be fully transparent, semi-transparent, or may be optically opaque. In some embodiments, the transparency of shield 200 is altered by varying the base material of shield 200 and/or by adding color/laser absorptive dies. In some embodiments, the addition of additional dies may not increase the thickness of shield 200. Further, absorptive and reflective coatings may be used on shield 200 to alter the transparency of shield 200.

Figure 9:
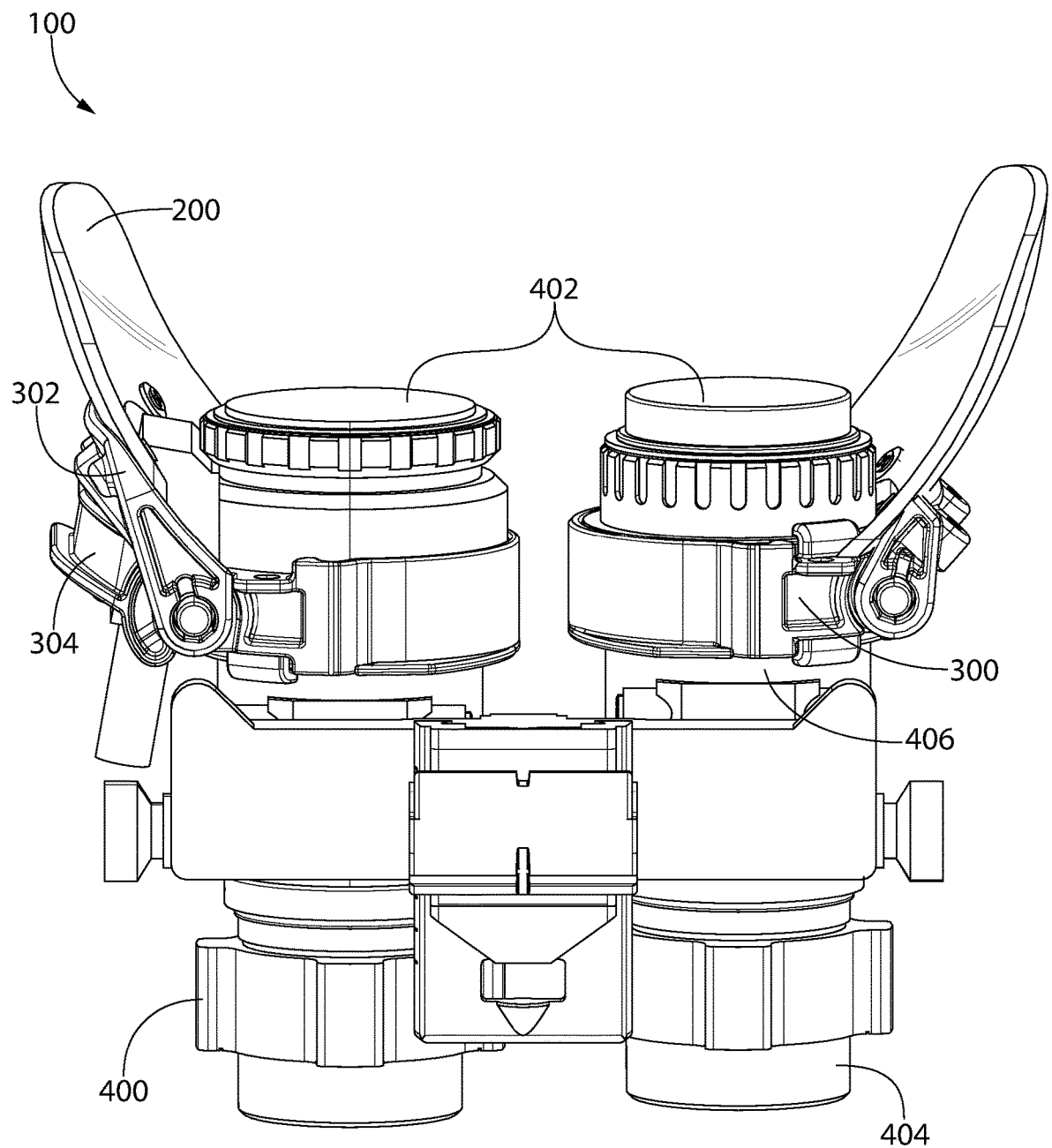
FIG. 9 is a top view of the pair of eye shields of FIG. 1.

Referring to FIG. 9, shield 200 may be secured to optical device 400 via attachment device 300. Shield 200 may be pivotally coupled to attachment device 300. Attachment device 300 may be disposed around optical device 400 to secure shield 200 to optical device 400. For example, attachment device 300 may be clamped around optical device 400 thereby securing shield 200 to optical device 400. In some embodiments, attachment device 300 is secured to optical device 400 via a locking draw-latch (e.g., locking element 310) configured to enable attachment device 300 to clamp around optical device 400. In some embodiments, attachment device 300 is comprised of polycarbonate, acrylonitrile butadiene styrene (ABS), polyethylene, or any combination thereof. Attachment device 300 may be comprised of nylon. In some embodiments, attachment device 300 is configured to be secured to optical device 400 without the use of tools. For example, a user may secure attachment device 300 to optical device 400 using their hands and may not require any tools or additional accessories to secure attachment device 300 to optical device 400.

In some embodiments, attachment device 300 can be coupled to optical device 400 when optical device 400 is in either the use position or stowed position. Attachment device 300 may be coupled to optical device 400 proximate eye piece 402. Attachment device 300 may be coupled to optical device 400 further away from the user's face, thereby coupling shield 200 to optical device 400 away from eye piece 402. In some embodiments, attachment device 300 couples to optical device 400 between eye piece 402 and objective lens 404 to couple shield 200 to optical device 400 between eye piece 402 and objective lens 404. For example, optical device 400 may include tube 406 disposed between eye piece 402 and objective lens 404, and attachment device 300 may secure shield 200 to tube 406 of optical device 400. Attachment device 300 may secure shield 200 to tube 406 to allow for adjustment of eye piece 402 as necessary without interfering or disturbing shield 200. For example, eye piece 402 may include an adjustment mechanism and thus coupling of attachment device 300 to eye piece 402 would render the adjustment mechanism inoperable or difficult to use. Therefore, attachment device 300 may couple shield 200 to tube 406, proximate eye piece 402 such that eye piece 402 is not rendered difficult to reach and shield 200 remains proximate the user's eyes.

Figure 10A:
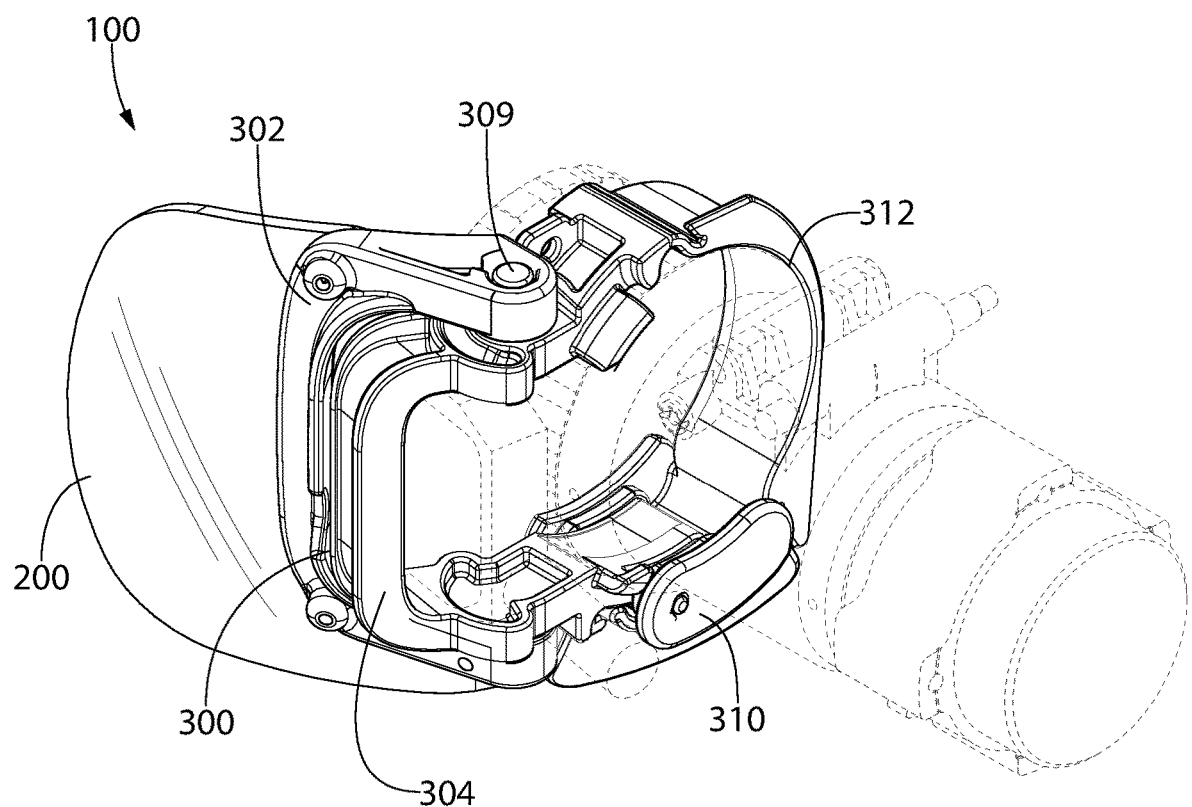
FIG. 10A is a right-side perspective view of a right eye shield of the pair of eye shields of FIG. 1.
Figure 10B:
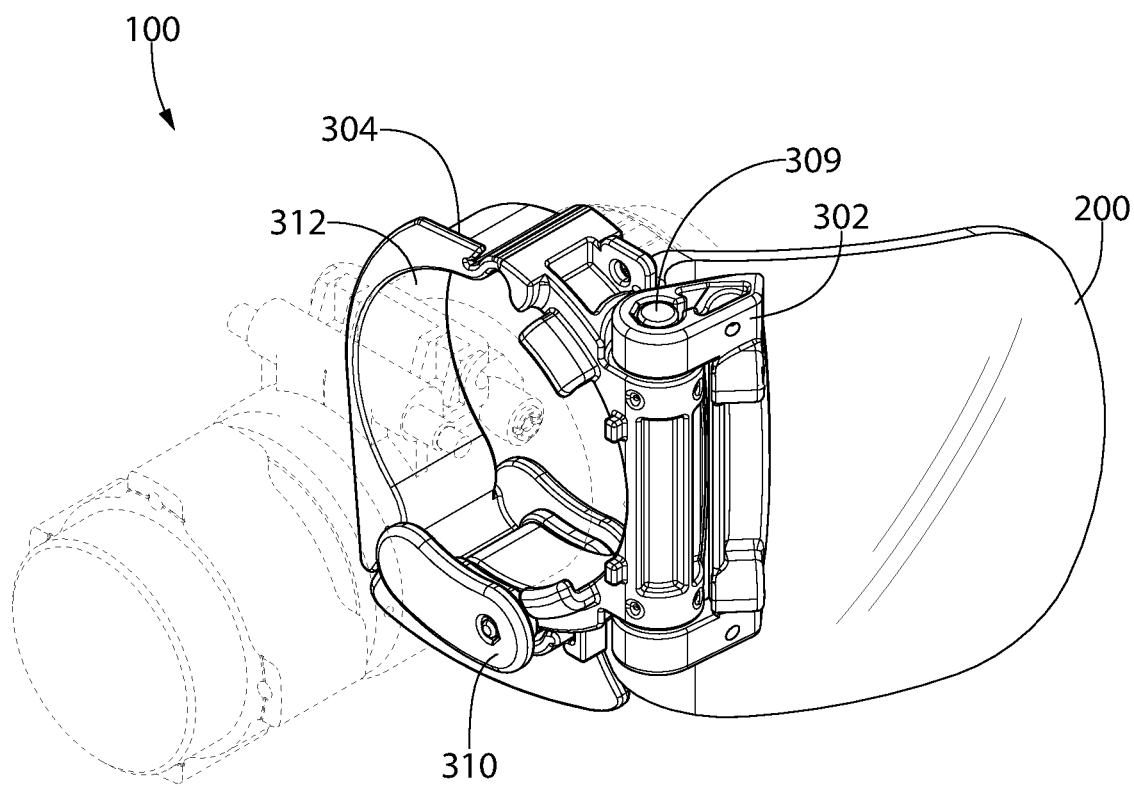
FIG. 10B is a left-side perspective view of a left eye shield of the pair of eye shields of FIG. 1.

Referring to FIGS. 10A and 10B, attachment device 300 may include coupling mechanism 302, clamping ring 304, and locking element 310. Coupling mechanism 302 may be configured to pivotally couple shield 200 to clamping ring 304 thereby allowing shield 200 to pivot relative to optical device 400 when attachment device 300 is coupled to optical device 400. In some embodiments, shield 200 is coupled to attachment device 300 only at coupling mechanism 302. For example, shield 200 may be coupled to clamping ring 304 indirectly via coupling mechanism 302 and may not be directly coupled to clamping ring 304. In some embodiments, shield 200 is coupled to only a portion of clamping ring 304. In some embodiments, shield 200 is configured to partially surround clamping ring 304. For example, shield 200 may be configured to only surround a portion of clamping ring 304 without surrounding the entirety of clamping ring 304.

Clamping ring 304 may be secured around optical device 400 and secured in place via locking element 310. In some embodiments, clamping ring 304 is disposed around the entire circumference of tube 406 of optical device 400. For example, clamping ring 304 may include an open position and closed position, such that in the open position clamping ring 304 can be movable about tube 406 of optical device 400 and moved to the closed position to secure clamping ring 304 to a specific location on tube 406 of optical device 400.

In some embodiments, clamping ring 304 is secured in the closed position around optical device 400 by locking element 310. Locking element 310 may be configured to prevent clamping ring 304 from moving from the closed position to the open position and thus prevents decoupling from optical device 400. For example, locking element 310 may secure clamping ring 304 in the closed positioned thereby securing clamping ring 304, coupling mechanism 302, and shield 200 to optical device 400 during use. During use, engaging locking element 310 results in decreasing the diameter of clamping ring 304 thereby fixing it in place on tube 406.

In some embodiments, shield 200 is coupled to coupling mechanism 302, which is pivotally coupled to clamping ring 304, thereby pivotally coupling shield 200 to optical device 400 when attachment device 300 is coupled to optical device 400. Shield 200 may be fixedly or removably coupled to coupling mechanism 302. For example, shield 200 may be fixedly coupled to coupling mechanism 302 via fasteners, screws, magnets, adhesives, heating, hook-and-loop fasteners, or any other coupling mechanism desired. In some embodiments, shield 200 is fixedly coupled to coupling mechanism 302 to prevent shield 200 from inadvertently de-coupling from attachment device 300 during use. However, shield 200 may be removably coupled to coupling mechanism 302 such that shield 200 may be easily replaced if shield 200 becomes damaged.

In some embodiments, coupling mechanism 302 may be pivotally coupled to clamping ring 304. For example, coupling mechanism 302 may be configured to pivot about pivot point 309 thereby allowing shield 200 to pivot about pivot point 309. In some embodiments, pivot axis 220 extends through pivot point 309. Pivot axis 220 may be the axis about which shield 200 pivots/rotates. Coupling mechanism 302 pivoting about pivot point 309 allows shield 200 to fold away and towards the user's face during use. For example, shield 200 and coupling mechanism 302 may pivot away and towards optical device 400 to allow shield 200 to fold towards optical device 400 or towards the user's face. In some embodiments, coupling mechanism 302 may be hingedly coupled to clamping ring 304. For example, coupling mechanism 302 may include one or more hinges, which may be coupled to clamping ring 304 to allow coupling mechanism 302 and shield 200 to rotate about clamping ring 304. However, coupling mechanism 302 may be coupled to clamping ring 304 by magnets, fasteners, hinges, or any other coupling mechanism that allows coupling mechanism 302 and shield 200 to pivot and/or rotate about clamping ring 304.

Figure 11A:
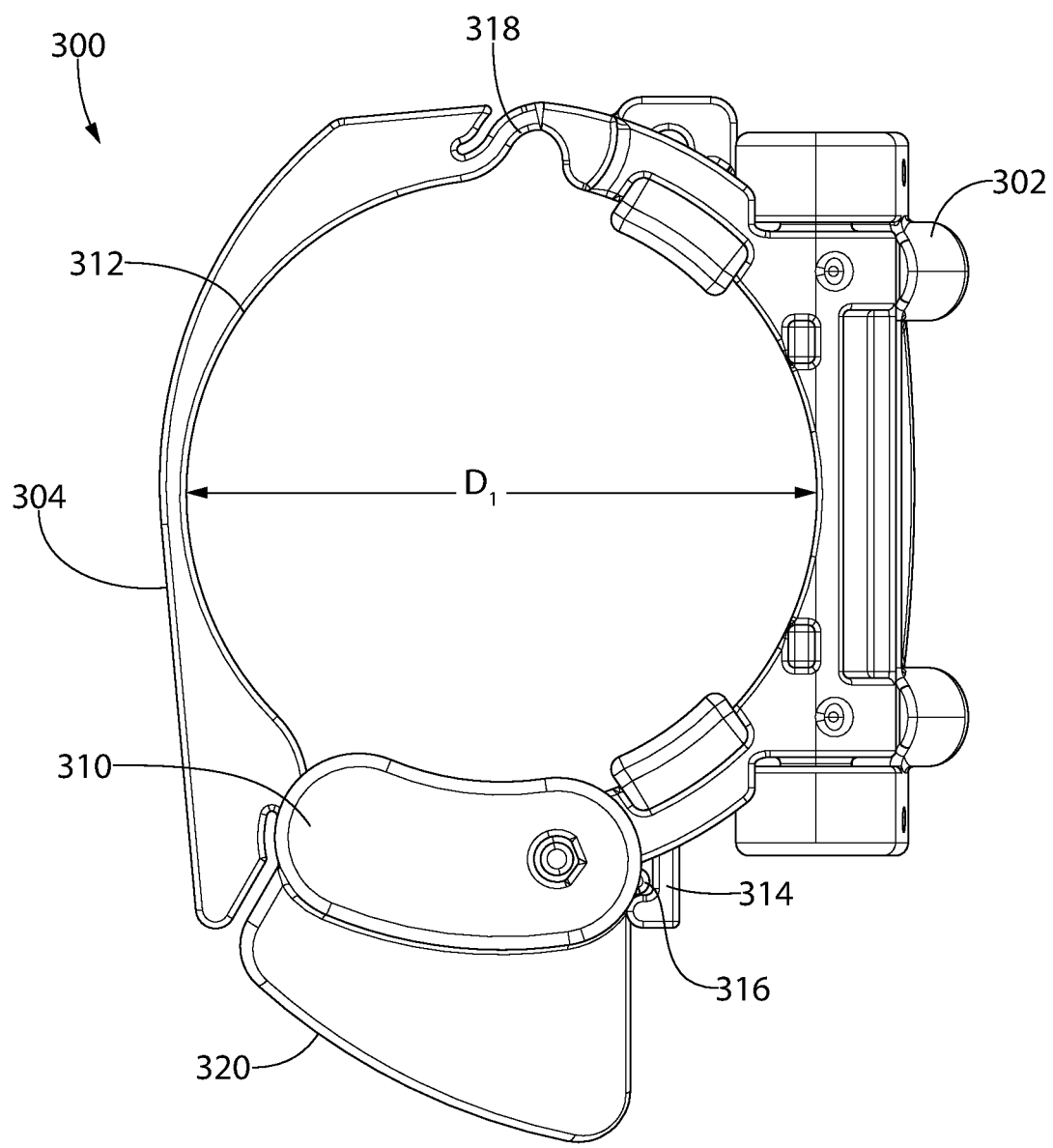
FIG. 11A is a front view of an exemplary clamping ring of the eye shield of FIG. 1.
Figure 11B:
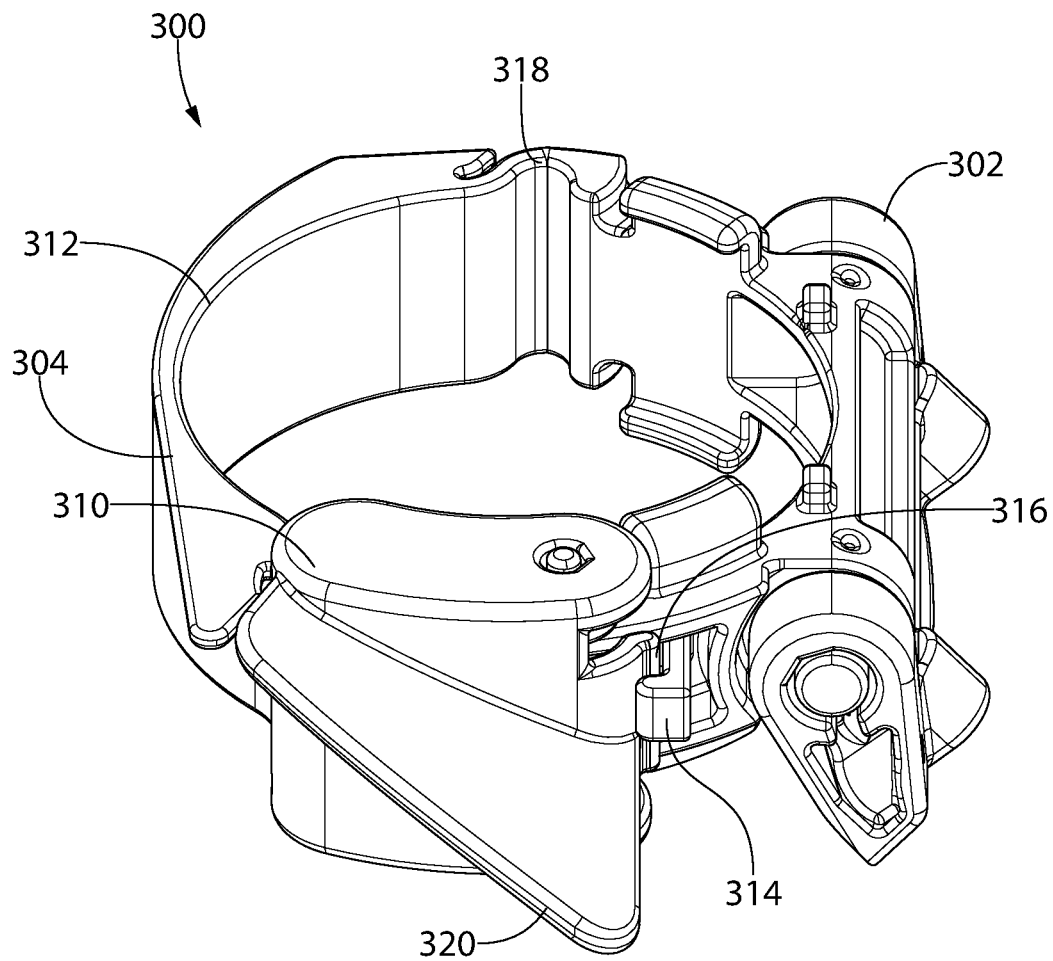
FIG. 11B is a perspective bottom view of the clamping ring of FIG. 11A.
Figure 11C:
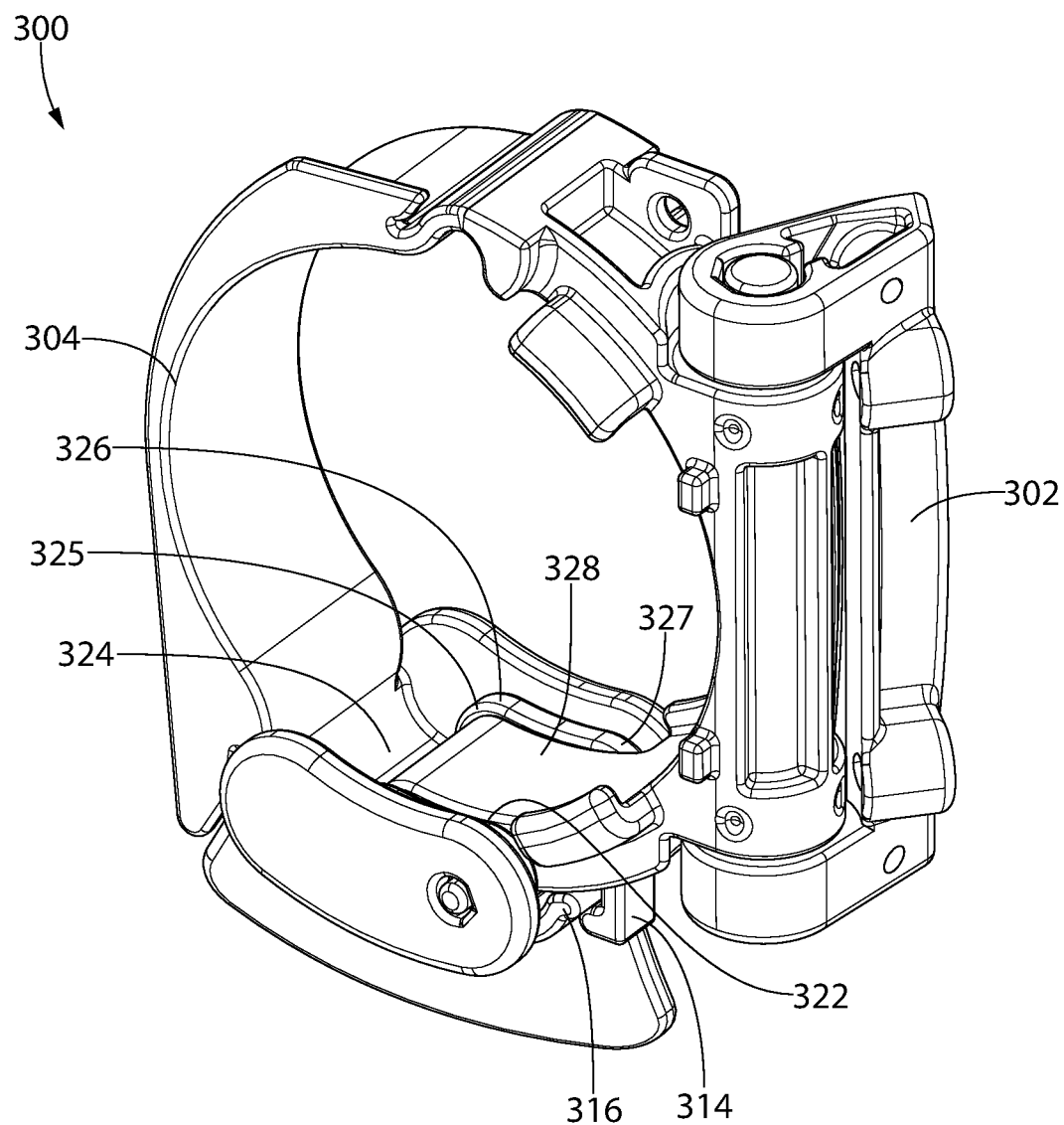
FIG. 11C is a front perspective view of the clamping ring of FIG. 11A.

Referring to FIGS. 11A-11C, attachment device 300 may include clamping ring 304. Clamping ring 304 may disposed around optical device 400 to secure shield 200 to optical device 400. For example, clamping ring 304 may be disposed around a substantial portion or the entirety of the outer circumference of tube 406 to ensure secure attachment of shield 200 and coupling mechanism 302 to optical device 400. In some embodiments, clamping ring 304 secures shield 200 and coupling mechanism 302 to optical device 400 to enable eye shield 100 to withstand high velocity winds, contact, or impact without decoupling from optical device 400. For example, during testing of eye shield 100, eye shield 100 remained secured in place and coupled to optical device 400 when exposed to 250 miles per hour (MPH) or 217 calibrated airspeed in knots (KCAS).

Clamping ring 304 may include aperture 312 and locking element 310. In some embodiments, clamping ring 304 has an open position and a closed position. Clamping ring 304 may be secured in the closed position via locking element 310. For example, clamping ring 304 may be configured to flex and bend at flex point 318 to assist clamping ring 304 in moving from an open position to a closed position. To move clamping ring 304 from the closed position to the open position, locking element 310 may have to be disengaged and moved from a locked position to an unlocked position.

In some embodiments, aperture 312 includes diameter $D_1$. Diameter $D_1$ of aperture 312 when clamping ring 304 is in the open position may be greater than when clamping ring 304 is in the closed position thereby allowing clamping ring 304 to be easily movable about tube 406 when clamping ring 304 is in the open position. In some embodiments, moving clamping ring 304 to the closed position results in a decrease in diameter $D_1$. In some embodiments, diameter $D_1$ of aperture 312 when clamping ring 304 is in the closed position is substantially the same as the diameter of tube 406 to ensure clamping ring 304 is secured around tube 406. Diameter $D_1$ of aperture 312 may be approximately 2 and ⅛ inches when clamping ring 304 is in the open position and approximately 1 and ⅞ inches when clamping ring 304 is in the closed position. However, diameter $D_1$ of aperture 312 may be approximately 1 inch to approximately 5 inches when clamping ring 304 is in the open position and between approximately 0.1 inches and approximately 4 inches when clamping ring 304 is in the closed position. Clamping ring 304 and aperture 312 may be sized and shaped to fit around the outer circumference of tube 406 of optical device 400. For example, aperture 312 may be sized and shaped to fit securely around the entirety of the outer circumference of tube 406 of optical device 400. In some embodiments, aperture 312 is substantially circular. However, aperture 312 may be any shape or size desired to fit around the outer circumference of tube 406.

In some embodiments, locking element 310 is configured to secure clamping ring 304 in the closed position. Locking element 310 may be locking draw-latch. Locking element 310 may have an unlocked position and locked position. When locking element 310 is in the unlocked position, clamping ring 304 may be in the open position. For example, clamping ring 304 may be biased to be in the open position when locking element 310 is in the unlocked position. Further, when locking element 310 is in the locked position, clamping ring 304 may be in the closed position. Clamping ring 304 may be secured in the closed position by engaging locking element 310 such that locking element 310 is in the locked position. To move clamping ring 304 from the closed position to the open position, locking element 310 may be released and disengaged and placed in the unlocked position. In some embodiments, clamping ring 304 being in the closed position and locking element 310 being in the locked position ensures that attachment device 300 is secured around optical device 400 (e.g., tube 406 of optical device 400), thereby securing shield 200 to optical device 400. Locking element 310 may be secured in the locked position by a press fitting mechanism, latch mechanism, magnets, friction fitting mechanism, a motor, or any other mechanism capable of securing locking element 310 in the locked position.

In some embodiments, when locking element 310 is unlocked and clamping ring 304 is in the open position, diameter $D_1$ of aperture 312 is greater than when clamping ring 304 is in the closed position. For example, clamping ring 304 may be configured to bend and/or flex at flex point 318 to be in the open position thereby increasing diameter $D_1$ of aperture 312. Clamping ring 304 may be in the open position to secure clamping ring 304 around optical device 400. For example, locking element 310 may be unlocked and clamping ring 304 may be in the open position thereby increasing diameter $D_1$ of aperture 312 such the clamping ring 304 can be easily placed around tube 406 of optical device 400.

In some embodiments, locking element 310 may include extending member 322 and channel 324. Extending member 322 and channel 324 may be disposed opposite flex point 318. However, extending member 322 and channel 324 may be located anywhere on clamping ring 304 or attachment device 300. In some embodiments, channel 324 is configured to slidably receive extending member 322. For example, when clamping ring 304 is moved from the open position to the closed position, extending member 322 may slide into channel 324. Channel 324 may receive extending member 322 when clamping ring 304 moves from the open position to the closed position. In some embodiments, extending member 322 being disposed within channel 324 allows locking element 310 to be engaged and thus in the locked position.

In some embodiments, extending member 322 is coupled to channel 324 via one or more coupling elements 326. For example, coupling element 326 may couple extending member 322 to channel 324 such that when clamping ring 304 is in the open position and locking element 310 is unlocked, extending member 322 is no longer disposed within channel 324, but is disposed adjacent channel 324. However, extending member 322 may be directly coupled to channel 324 such that when locking element 310 is unlocked, extending member 322 is only partially disposed within channel 324. Attachment device 300 may include one coupling element 326 or more than coupling element 326. For example, attachment device 300 may include two coupling elements 326 disposed on either side of extending member 322 such that both coupling elements 326 coupled extending member 322 to channel 324.

With continued reference to FIGS. 11A-11C, when clamping ring 304 is in the open position, extending member 322 may not be disposed with channel 324, but may still be coupled to channel 324 via coupling element 326. Coupling element 326 allows extending member 322 to be coupled to channel 324 regardless of whether clamping ring 304 is in the open position or the closed position. When clamping ring 304 moves from the closed position to the open position, both extending member 322 and channel 324 may pivot about coupling element 326 and away from each other. In some embodiments, extending member 322 is pivotally coupled to coupling element 326 at first end 325 and channel 324 is coupled to coupling element 326 at second end 327. First end 325 may be opposite second end 327 to allow extending member 322 and channel 324 to pivot and rotate away from each other when clamping ring 304 is moved from the closed position to the open position.

Coupling element 326 may include groove 328. In some embodiments, groove 328 is sized and shaped to receive extending member 322. For example, when clamping ring 304 is in the closed position, extending member 322 may be disposed within groove 328, which may be disposed within channel 324. Upon opening of clamping ring 304, extending member 322 may move out of groove 328 and coupling element 326 may rotate such that groove 328 is inverted compared to when clamping ring 304 is in the closed position. In some embodiments, coupling element 326 is configured to rotate about second end 327. For example, when clamping ring 304 is in the closed position, coupling element 326 is disposed within channel 324 and groove 328 is in a base position such that extending member 322 is disposed within groove 328. When clamping ring 304 is moved to the open position, coupling element 326 may rotate about second end 327 such that groove 328 is inverted compared to the base position resulting in extending member 322 rotating about first end 325 and no longer being disposed within groove 328. In some embodiments, when clamping ring 304 is in the open position, extending member 322, coupling element 326, and channel 324 are serially coupled. Extending member 322, coupling element 326, and channel 324 may be serially coupled such that a portion of extending member 322 is disposed within coupling element 326 (e.g., groove 328), and a portion of coupling element 326 is disposed within channel 324.

In some embodiments, coupling element 326 is configured to assist locking of locking element 310. For example, when clamping ring 304 is in the closed position, coupling element 326 may be disposed between extending member 322 and channel 324. In some embodiments, coupling element 326 is disposed between extending member 322 and channel 324 such that extending member 322 is friction fitted within channel 324 to secure extending member 322 within channel 324, and thus securing clamping ring 304 in the closed position. In some embodiments, attachment device 300 includes two coupling elements 326 and channel 324 has a width substantially equal to the sum of the width of extending member 322 and the thickness of both coupling elements 326.

Referring to FIGS. 12A-12B, when clamping ring 304 is in the open position, coupling element 326 may extend from channel 324 to extending member 322. For example, when clamping ring 304 is in the open position, diameter $D_1$ may increase and extending member 322 may be disposed out of and away from channel 324. When clamping ring 304 is moved to the closed position, diameter $D_1$ may decrease and extending member 322 may move towards or may be at least partially disposed within channel 324. In some embodiments, when clamping ring 304 is in the open position, channel 324 is coupled to coupling element 326, which is coupled to extending member 322.

Referring to FIGS. 11A-12B, locking element 310 may include latch 314 and lip 316. Lip 316 may be secured in place by latch 314 to secure locking element 310 in the locked position and prevent rotation or movement of locking element 310. For example, lip 316 may be secured against latch 314 when clamping ring 304 is in the closed position and locking element 310 is in the locked position, thereby securing clamping ring 304 in the closed position and around tube 406 of optical device 400. In some embodiments, lip 316 is disposed at the entrance of channel 324 and latch 314 is disposed on extending member 322. Coupling element 326 may assist is guiding lip 316 to latch 314 by limiting the rotational movement of channel 324 away from extending member 322. For example, channel 324 may pivot about coupling element 326 such that channel 324 abuts extending member 322 as clamping ring 304 moves to the closed position. When channel 324 abuts extending member 322, lip 316 may abut latch 314. When pressure is applied to clamping ring 304 causing channel 324 to push towards extending member 322, lip 316 may be pushed against latch 314 and may be secured by latch 314 in a locked position.

In some embodiments, coupling element 326 is biased to dispose extending member 322 within channel 324. Coupling element 326 being biased to keep extending member 322 disposed within channel 324 results in clamping ring 304 being easily moved from the open position to the closed position. For example, in use, when clamping ring 304 is in the open position, a user may need to only apply light pressure to channel 324 to cause coupling element 326 to rotate and thus cause extending member 322 to move towards channel 324. Coupling element 326 rotating causes extending member 322 to become disposed within channel 324, thereby engaging locking element 310 in the locked position.

In practice, as clamping ring 304 is moved from the open position to the closed position, channel 324 may pivot about extending member 322 via coupling element 326 and may slidably receive extending member 322 resulting in lip 316 moving towards latch 314. Latch 314 may be biased towards lip 316 and movement/pushing of lip 316 against latch 314 results in latch 314 moving slightly away from lip 316 prior to receiving and securing lip 316. Once lip 316 moves past latch 314, latch 314 may return to the biased position towards lip 316. Latch 314 returning to the biased position may prevent lip 316 from further movement thereby securing lip 316 within latch 314 and securing locking element 310 in the locked position. In some embodiment, locking element 310 being secured in the locked position results in securing clamping ring 304 in the closed position and thus preventing inadvertent opening of clamping ring 304, which assists in securing clamping ring 304 to optical device 400.

In some embodiments, locking element 310 is unlocked by moving latch 314 to release lip 316. For example, pressure may be applied to latch 314 to move latch 314 against its biased position. Applying pressure to latch 314 moves latch 314 away from lip 316, thereby releasing lip 316 and allowing channel 324 to pivot and rotate away from extending member 322. In some embodiments, extending member 322 is configured to pivot and rotate away from channel 324.

In some embodiments, locking element 310 may include tab 320. Tab 320 may be sized and shaped to allow a user to rest their finger against tab 320 as they push against latch 314. Tab 320 may be coupled to lip 316 and may extend away from lip 316. In use, tab 320 acts as a guide to direct a user's finger towards latch 314. For example, tab 320 may be ergonomically shaped to easily guide a user's finger towards latch 314 for unlocking locking element 310. Tab 320 may extend at an angle relative to locking element 310 to comfortably allow a user to rest their finger against tab 320 as they push against latch 314. In some embodiments, a user may pull down on tab 320 to disengage lip 316 from latch 314. For example, a user may grip and pull downwards on tab 320 resulting in lip 316 pushing against latch 314 and moving away from latch 314, thereby unlocking locking element 310. A user may push against or apply pressure to latch 314 via tab 320 to release lip 316, thereby placing locking element 310 in the unlocked position and placing clamping ring 304 in the open position. Once a user no longer applies pressure to latch 314, latch 314 may return to its biased position. When locking element 310 is unlocked, channel 324 may be disposed below extending member 322, while remaining coupled to extending member 322 via coupling element 326. In some embodiments, when locking element 310 is unlocked, channel 324 is adjacent extending member 322 such that channel 324 is below and proximate extending member 322.

Figure 13A:
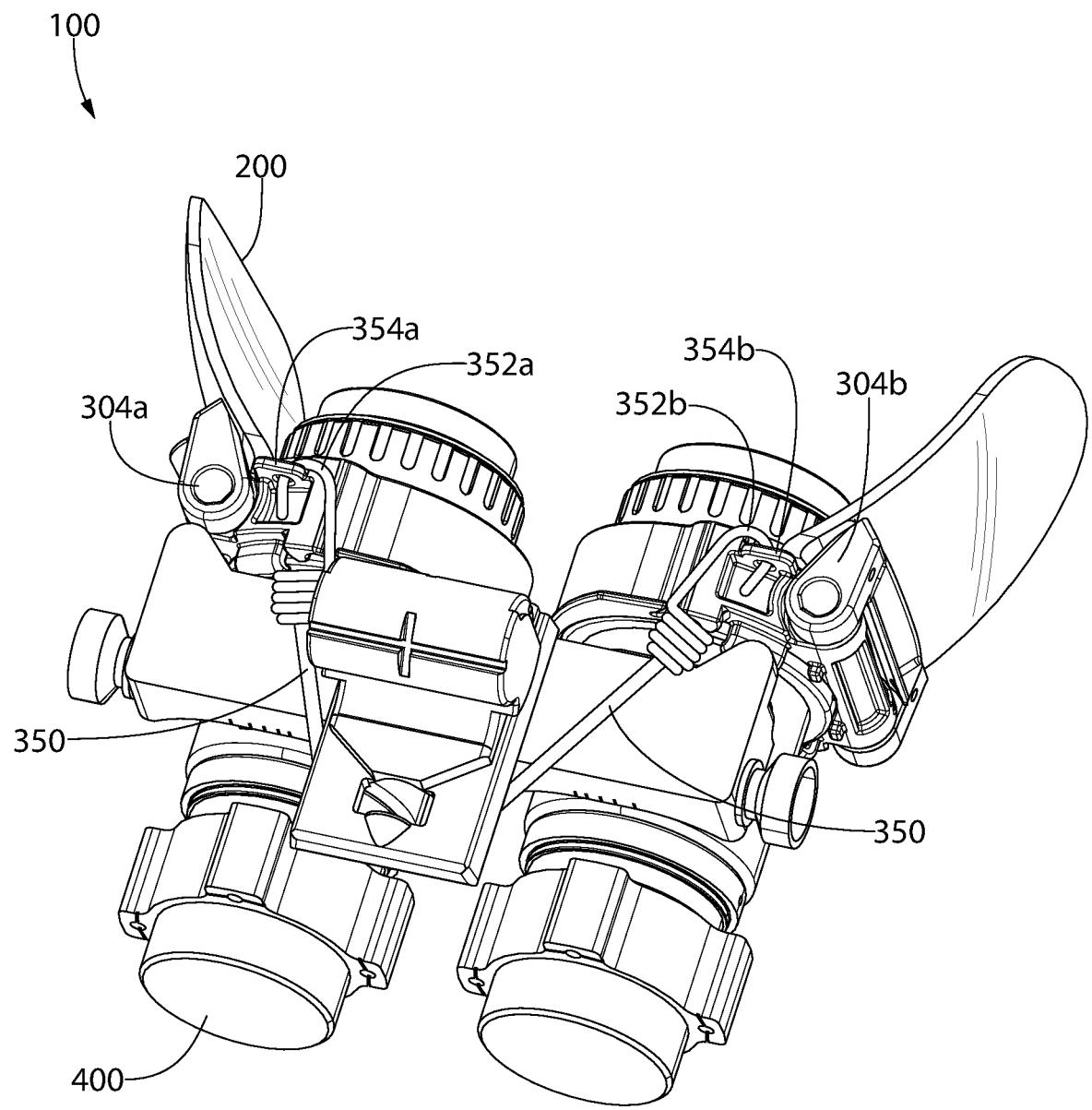
FIG. 13A is top perspective view of a pair of eye shields including a tethering system in accordance with an exemplary embodiment of the present invention shown mounted to an optical device.
Figure 13B:
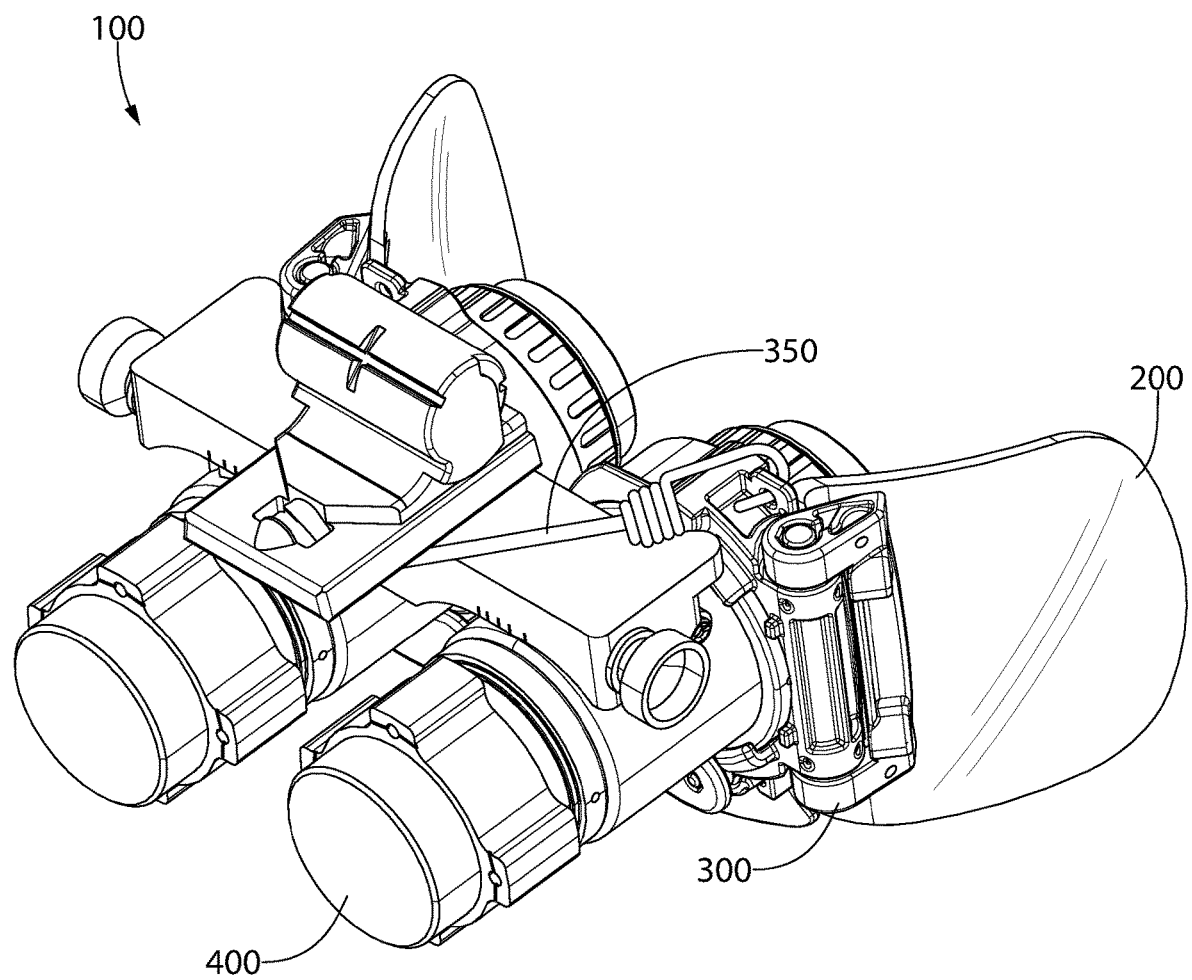
FIG. 13B is right-side perspective view of the pair of eye shields of FIG. 13A.

Referring to FIGS. 13A and 13B, eye shield 100 may include one or more tethers 350. Tethers 350 may be configured to couple eye shield 100 to an optical device. For example, tether 350 may be coupled to clamping rings 304a, 304b to secure attachment device 300, and shield 200, to optical device 400. Clamping rings 304a and 304b are similar to clamping ring 304 shown in FIGS. 10A-12B and as discussed herein except clamping rings 304a and 304b include attachment points 352a and 352b, respectively. Tether 350 may be coupled to clamping ring 304a at attachment point 352a, wrapped around optical device 400, and then coupled to clamping ring 304b at attachment point 352b to secure attachment device 300 to optical device 400. However, multiple tethers 350 may be used to couple each of clamping rings 304a, 304b individually to optical device 400 via attachment points 352a, 352b. For example, eye shield 100 may include one or more tethers 350 to secure attachment device 300 to optical device 400. Tether 350 may be removable from clamping ring 304 or may be fixed to clamping ring 304. However, tether 350 may be coupled to eye shield 100 at any other location.

In some embodiments, each eye shield 100 includes one or more tethers 350. Tethers 350 may be configured to couple two eye shields 100 together (e.g., to each other). For example, a first tether may be coupled to a first eye shield and a second tether may be coupled to a second eye shield, and the first tether may be coupled to the second tether to couple the first eye shield to the second eye shield. Tether 350 may be coupled to clamping ring 304 of each eye shield 100 at one end and coupled to each other at the other end to couple one eye shield 100 to an adjacent eye shield 100.

Tether 350 may be used to prevent foreign object damage hazards. For example, one shield 200 may be tethered to another adjacent shield 200 via tether 350 configured to wrap around optical device 400. In some embodiments, tethering one shield 200 to another adjacent shield 200 reduces the risk of shields 200 being lost or dropped when handled or in use. In practice, one or more tethers 350 may be used to prevent inadvertent decoupling of attachment device 300 from optical device 400. However, eye shield 100 may include magnets, fasteners, hook-and-loop fasteners, adhesives, or any other coupling mechanism to secure attachment device 300 to optical device 400.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. The words "proximal" and "distal" designate directions in the drawings to which reference is made. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

What is claimed is:

1. An eye shield comprising:
an attachment device configured to be coupled to an optical device, the attachment device including a clamping ring having an open position and a closed position;
a shield coupled to the clamping ring to pivot away and towards the clamping ring, the shield extending laterally from the attachment device; and
a locking element disposed on the clamping ring configured to lock the clamping ring in the closed position, wherein the locking element has a locked and an unlocked position, and the locking element being in the locked position results in the clamping ring being in the closed position,
wherein the clamping ring includes an aperture having a diameter, the diameter of the aperture being greater when the clamping ring is in the open position than when the clamping ring is in the closed position.

2. The eye shield of claim 1 further comprising:
a coupling mechanism coupling the shield to the clamping ring.

3. The eye shield of claim 2, wherein the shield is fixedly coupled to the coupling mechanism.

4. The eye shield of claim 2, wherein the coupling mechanism is pivotally coupled to the clamping ring to allow the shield and the coupling mechanism to pivot relative to the clamping ring.

5. The eye shield of claim 2, wherein the coupling mechanism is coupled to the clamping ring via at least one pivot pin.

6. The eye shield of claim 1, wherein the locking element includes a channel and an extending member, the channel sized and shaped to receive the extending member.

7. The eye shield of claim 6, wherein the locking element includes a coupling element coupling the channel to the extending member.

8. The eye shield of claim 6, wherein the channel includes a lip and the extending member includes a latch, the latch configured to receive and secure the lip in place when the extending member is disposed within the channel.

9. The eye shield of claim 8, wherein the latch is configured to be actuated by a user to move the locking element from the locked position to the unlocked position.

10. The eye shield of claim 1, wherein the locking element includes a tab extending away from the clamping ring.

11. The eye shield of claim 1, wherein the shield is pivotally coupled to the clamping ring.

12. The eye shield of claim 1, wherein the locking element includes a lip and a latch, the latch configured to secure the lip in place when the locking element is in the locked position.

13. The eye shield of claim 1, wherein the attachment device and the shield are composed of different materials.

14. The eye shield of claim 1, wherein the shield is optically transparent.

15. The eye shield of claim 1, wherein the shield is optically opaque to lasers and/or lights.

16. The eye shield of claim 1, wherein the clamping ring is configured to be disposed around a portion of the optical device, the optical device including one of night vision goggles, binoculars, monocular, scopes, spectacles, augmented reality system, virtual reality system, display devices, or cameras.

17. The eye shield of claim 1 further comprising:
   a first tether coupled to the attachment device and configured to couple to a second tether coupled to an adjacent attachment device to secure the attachment device to the adjacent attachment device.

18. An eye shield comprising:
   an attachment device configured to be coupled to an optical device, the attachment device including a clamping ring having an open position and a closed position, and a coupling mechanism pivotally coupled to the clamping ring;
   a shield coupled to the coupling mechanism and configured to pivot away and towards the clamping ring, the shield extending laterally from the attachment device; and
   a locking element disposed on the clamping ring configured to lock the clamping ring in the closed position around at least a portion of the optical device, the locking element having a locked and an unlocked position, and the locking element being in the locked position results in the clamping ring being in the closed position,
   wherein the locking element including a lip and a latch, the latch configured to secure the lip in place when the locking element is in the locked position.

19. An eye shield comprising:
   an attachment device configured to be coupled to an optical device, the attachment device including a clamping ring having an open position and a closed position, and a coupling mechanism pivotally coupled to the clamping ring;
   a shield coupled to the coupling mechanism and configured to pivot away and towards the clamping ring, the shield extending laterally from the attachment device and being optically opaque to lasers and/or light; and
   a locking element disposed on the clamping ring configured to lock the clamping ring in the closed position around the optical device, the locking element having a locked and an unlocked position, the locking element being in the locked position results in the clamping ring being in the closed position,
   wherein the locking element includes a tab extending from the locking element, a channel having a lip, and an extending member having a latch, the channel sized and shaped to receive the extending member and the latch configured to secure the lip in place when the locking element is in the locked position.

\* \* \* \* \*